(12) United States Patent
Kato et al.

(10) Patent No.: US 10,793,819 B2
(45) Date of Patent: Oct. 6, 2020

(54) LIQUID INJECTION METHOD

(71) Applicants: Kaneka Corporation, Osaka (JP); Kyoto University, Kyoto (JP)

(72) Inventors: Tomohisa Kato, Hyogo (JP); Kazuya Hamada, Hyogo (JP); Haruhisa Inoue, Kyoto (JP); Takayuki Kondo, Kyoto (JP)

(73) Assignees: KANEKA CORPORATION, Osaka (JP); KYOTO UNIVERSITY, Kyoto (JP)

( * ) Notice: Subject to any disclaimer, the term of this patent is extended or adjusted under 35 U.S.C. 154(b) by 88 days.

(21) Appl. No.: 15/850,856

(22) Filed: Dec. 21, 2017

(65) Prior Publication Data
US 2018/0135002 A1    May 17, 2018

Related U.S. Application Data

(63) Continuation of application No. PCT/JP2016/068925, filed on Jun. 24, 2016.

(30) Foreign Application Priority Data

Jun. 25, 2015 (JP) .................. 2015-127698

(51) Int. Cl.
| | | |
|---|---|---|
| *C12M 3/06* | (2006.01) | |
| *G01N 33/50* | (2006.01) | |
| *G01N 33/68* | (2006.01) | |
| *C12M 1/00* | (2006.01) | |

(52) U.S. Cl.
CPC ............ *C12M 27/16* (2013.01); *C12M 29/00* (2013.01); *C12M 29/06* (2013.01); *C12M 29/14* (2013.01); *C12M 29/26* (2013.01); *G01N 33/5032* (2013.01); *G01N 33/5058* (2013.01); *G01N 33/6896* (2013.01); *G01N 2800/2835* (2013.01)

(58) Field of Classification Search
CPC ...... C12M 29/00; C12M 29/06; C12M 29/14; C12M 29/26; G01N 33/5032; G01N 33/5058; G01N 33/6896; G01N 2800/2835
USPC ......................................................... 435/395
See application file for complete search history.

(56) References Cited

FOREIGN PATENT DOCUMENTS

| | | | |
|---|---|---|---|
| JP | 2004-154027 A | | 6/2004 |
| JP | 2004-236547 | * | 8/2004 |
| JP | 2004-236547 A | | 8/2004 |
| JP | 2004-261133 | * | 9/2004 |
| JP | 2004-261133 A | | 9/2004 |
| JP | 2006-141328 A | | 6/2006 |
| JP | 4293518 B2 | | 7/2009 |
| JP | 2013-017461 A | | 1/2013 |
| JP | 2013-520960 A | | 6/2013 |
| JP | 2014-027941 A | | 2/2014 |
| JP | 2014-068579 A | | 4/2014 |
| JP | 2014-087352 A | | 5/2014 |
| JP | 2015-506905 A | | 3/2015 |
| WO | 2014/148646 A1 | | 9/2014 |

OTHER PUBLICATIONS

International Search Report issued in International Application No. PCT/JP2016/068925; dated Aug. 2, 2016 (2 pages).

\* cited by examiner

*Primary Examiner* — Jennifer M. H. Tichy
(74) *Attorney, Agent, or Firm* — Osha Liang LLP

(57) ABSTRACT

A liquid injection method for injecting a liquid into a culture vessel includes tilting the culture vessel around a horizontal axis at a tilt angle (X°) of greater than 0° and 50° or less, wherein adherent cells are adhered to the culture vessel; and injecting the liquid into the culture vessel at a predetermined linear velocity (Y mm/s) via a wall surface of the culture vessel tilted at the tilt angle (X°), wherein the tilt angle (X) and the linear velocity (Y) satisfy the following (formula 1): $Y \leq 5.075X + 123$ (formula 1).

7 Claims, 4 Drawing Sheets

LIQUID INJECTION METHOD

TECHNICAL FIELD

One or more embodiments of the present invention relate to a liquid injection method for injecting a required liquid into a culture vessel to which adherent cells or an adherent cell population is attached, a method for efficiently culturing adherent cells or an adherent cell population by using the liquid injection method, a method for efficiently screening a growth factor or a nutritional factor useful for culture of adherent cells or an adherent cell population by using the liquid injection method, a method for efficiently evaluating toxicity of a test substance to adherent cells or an adherent cell population by using the liquid injection method, and a method for efficiently screening a test substance having therapeutic efficacy for a nervous system disease, a neurodegenerative disease, or Alzheimer-type dementia by using the liquid injection method.

BACKGROUND iPS cell (induced pluripotent stem cell)-derived nerve cells (see, for example, Patent Literature 1) are useful over a wide range such as drug discovery screening and safety evaluation of drugs and food.

Culture of adherent (adhesive) cells, such as iPS cell-derived nerve cells, is carried out in a state where the cells are attached (adhered) to the bottom surface of a culture vessel, and a medium, a washing solution such as a phosphate-buffered saline (PBS), and a detachment solution such as trypsin are injected into the culture vessel (see, for example, Patent Literature 2).

Here, in the culture vessel (incubator 38) of Patent Literature 2, a tube connection member 19 for injecting a liquid such as a medium is provided at the center of the vessel, and a tilt portion 381 is formed below the tube connection member 19. Thus, a liquid such as a medium injected from the tube connection member 19 falls via the tilt portion 381, whereby impact on culture cells due to the fall of the liquid is alleviated.

Moreover, as a culture solution replacing device for effectively performing an operation of replacing a culture solution into a culture vessel, there is a replacing device that performs such an operation in a state where a culture vessel is tilted (see, for example, Patent Literature 3).

Here, a culture vessel 14 of Patent Literature 3 has an opening 12 provided in a side surface thereof. In a state where the culture vessel 14 is tilted by vessel angle adjusting means 26 such that the opening 12 side of the culture vessel 14 is located at a high position, an injection pipe 18 and a discharge pipe 20 are inserted into the opening 12 and an operation of replacing a culture solution is performed.

CITATION LIST

Patent Literature

[PTL 1] Japanese Unexamined Patent Application Publication No. 2013-520960
[PTL 2] Japanese Unexamined Patent Application Publication No. 2006-141328
[PTL 3] Japanese Patent No. 4293518

However, the adherent cells such as iPS cell-derived nerve cells attached to the bottom surface of the culture vessel easily die due to a physical load upon injection of a liquid such as a medium and a PBS, and a decrease in cell number and variations occur when the adherent cells are used, so that it is difficult to acquire correct experiment and evaluation data; and particularly, iPS cell-derived nerve cells very easily cause cell death, for example, upon injection of a medium in a state where differentiation has progressed, and the adherent cells become unusable due to death of many adherent cells depending on the manner of injecting the liquid such as the medium.

The liquid injection method disclosed in Patent Literature 2 achieves an effect of being able to alleviate impact due to fall of a liquid to a certain extent, since the liquid falls via the tilt portion 381, which is formed in the culture vessel (incubator 38). However, the liquid injection method requires the culture vessel with a special shape having the tilt portion 381 and the tube connection member 19, and cannot handle a multi-dish or multi-well plate, etc.

In addition, in the liquid injection method disclosed in Patent Literature 3, the vessel angle adjusting means 26 for tilting the culture vessel 14 is provided. However, a culture solution is injected directly to culture cells from the injection pipe 18, which is inserted into the opening 12 in the side surface of the culture vessel 14, and thus impact due to fall of the liquid is directly transmitted to the culture cells. Therefore, it is difficult to apply the liquid injection method to adherent cells which easily die.

Furthermore, among conventional liquid injection methods, there seems to be no liquid injection method that focuses on improving operation efficiency while assuredly performing treatment such that culture cells do not die.

SUMMARY

One or more embodiments of the present invention provide a liquid injection method that, in injecting a liquid such as a medium to adherent cells or an adherent cell population within a culture vessel, can prevent cell death, which is a phenomenon specific to adherent cells, and thereby improve the survival rate of the adherent cells and that can improve operation efficiency.

In addition, one or more embodiments of the present invention provide: a method for efficiently culturing adherent cells or an adherent cell population by using the liquid injection method; a method for efficiently screening a growth factor or a nutritional factor useful for culture of adherent cells or an adherent cell population by using the liquid injection method; a method for efficiently evaluating toxicity of a test substance to adherent cells or an adherent cell population by using the liquid injection method; and a method for efficiently screening a test substance having therapeutic efficacy for a nervous system disease, a neurodegenerative disease, or Alzheimer-type dementia by using the liquid injection method.

As a result of conducting thorough research, the present inventors have found that the a physical load can be reduced by causing a tilt angle of a culture vessel and a linear velocity in injecting a liquid to satisfy a specific condition, thereby significantly reducing the rate of death of adherent cells.

One or more embodiments of the present invention include:

[1] A liquid injection method for injecting a required liquid into a culture vessel to which adherent cells or an adherent cell population is adhered, includes:
a culture vessel tilting step of tilting the culture vessel around a horizontal axis within a range of a tilt angle (X°) of greater than 0° and 50° or less from a state where the culture vessel is horizontal; and a liquid injection step of injecting the liquid at a predetermined linear velocity (Y mm/s) via a wall surface of the culture vessel tilted in the culture vessel tilting step, wherein a relationship between the tilt angle (X) and the linear velocity (Y) satisfies the following (formula 1):

$$Y \leq 5.075X + 123 \quad \text{(formula 1)}.$$

[2] In the liquid injection method according to [1], the tilt angle (X) is 30° or more and 40° or less.

[3] A method for culturing adherent cells or an adherent cell population, includes a step of sucking a medium in a culture vessel, and injecting a fresh medium into the culture vessel, thereby culturing the adherent cells or the adherent cell population. The liquid injection method according to [1] or [2] is used in injecting the fresh medium in the step.

[4] The method according to [3] further includes a washing step of washing an interior of the culture vessel by injecting a washing solution into the culture vessel and sucking the washing solution.

[5] In the method according to [4], the liquid injection method according to [1] or [2] is used in injecting the washing solution into the culture vessel in the washing step.

[6] The method according to any one of [3] to [5] further includes:

a cell detachment step of injecting a detachment solution to the adherent cells or the adherent cell population in the culture vessel and sucking the detachment solution with at least one of the adherent cells and the adherent cell population, which are detached;

a centrifugation step of injecting a cell suspension sucked in the cell detachment step into a centrifugation tube, and performing centrifugation with a centrifuge;

a cell number measurement and cell seeding amount adjustment step of removing a supernatant in the centrifugation tube having undergone the centrifugation step, sampling a part of the cell suspension obtained by injecting a medium into the centrifugation tube, measuring a cell number, and adjusting a cell number or a cell density for seeding the cells based on a result of the measuring; and a cell seeding step of seeding the cells having a required cell number adjusted in the cell number measurement and cell seeding amount adjustment step, into a culture vessel filled with the medium.

[7] In the method according to any one of [3] to [6], the medium contains a neurotrophic factor family.

[8] In the method according to [7], the neurotrophic factor family is at least one selected from the group consisting of Brain-derived Neurotrophic Factor (BDNF), Glial cell line-derived Neurotrophic Factor (GDNF), and Neurotrophin 3(NT-3).

[9] A method for screening a growth factor or a nutritional factor useful for culture of adherent cells or an adherent cell population, includes the steps of:

(a) bringing adherent cells or an adherent cell population into contact with test substances;

(b) culturing the adherent cells or the adherent cell population brought into contact with the test substances in the step (a), and adherent cells or an adherent cell population not brought into contact with the test substances, as a control, by the method according to any one of [3] to [8]; and (c) measuring cell numbers of the adherent cells or the adherent cell population obtained in the step (b), and selecting a test substance for which the cell number of the adherent cells or the adherent cell population brought into contact with the test substance is higher than the cell number of the control, as a growth factor or a nutritional factor useful for culture of the adherent cells or the adherent cell population.

[10] A method for evaluating toxicity to adherent cells or an adherent cell population, includes the steps of:

(d) bringing adherent cells or an adherent cell population into contact with test substances;

(e) culturing the adherent cells or the adherent cell population brought into contact with the test substances in the step (d), and adherent cells or an adherent cell population not brought into contact with the test substances, as a control, by the method according to any one of [3] to [8]; and (f) measuring cell numbers of the adherent cells or the adherent cell population obtained in the step (e), and evaluating a test substance for which the cell number of the adherent cells or the adherent cell population brought into contact with the test substance is lower than the cell number of the control, as having toxicity to the adherent cells or the adherent cell population.

[11] In the method according to any one of [1] to [10], the adherent cells or the adherent cell population is nerve cells.

[12] In the method according to [11], the nerve cells are obtained by inducing differentiation from induced pluripotent stem cells.

[13] In the method according to [12], the induced pluripotent stem cells are produced from somatic cells of a patient with a nervous system disease or somatic cells of a healthy individual into which a gene mutation causing the nervous system disease is introduced.

[14] A method for screening a substance having therapeutic efficacy for a nervous system disease, includes the steps of:

(g) bringing nerve cells into contact with test substances, (h) culturing the nerve cells brought into contact with the test substances in the step (g), and nerve cells not brought into contact with the test substances, as a control, by the method according to [7] or [8];

(i) measuring at least one of cell numbers and neurite lengths of the nerve cells obtained in the step (h), and selecting a test substance for which the cell number and/or the neurite length of the nerve cells brought into contact with the test substance is higher than the cell number of the control, as a substance having therapeutic efficacy for the nervous system disease.

[15] The method according to [14], further includes a step of inducing differentiation into nerve cells from induced pluripotent stem cells produced from somatic cells of a patient with the nervous system disease or somatic cells of a healthy individual into which a gene mutation causing the nervous system disease is introduced, and culturing the obtained nerve cells by the method according to [7] or [8], prior to the step (g).

[16] A method for screening a substance having therapeutic efficacy for a neurodegenerative disease due to protein misfolding, includes the steps of:

(j) bringing nerve cells derived from a patient with the neurodegenerative disease, into contact with test substances;

(k) culturing the nerve cells derived from the patient with the neurodegenerative disease and brought into contact with the test substances in the step (j) and nerve cells derived from the patient with the neurodegenerative disease and not brought into contact with the test substances, as a control, by the method according to [7] or [8]; and (l) measuring amounts of misfolded proteins in the nerve cells that are derived from the patient with the neurodegenerative disease and are obtained in the step (k) or in a medium thereof, and selecting a test substance for which the amount of the misfolded proteins in the nerve cells that are derived from the patient with the neurodegenerative disease and are brought into contact with the test substance or in the medium thereof is lower than the amount of the misfolded proteins of the control, as a substance having therapeutic efficacy for the neurodegenerative disease.

[17] A method for screening a substance having therapeutic efficacy for Alzheimer-type dementia, includes the steps of:

(m) bringing nerve cells of Alzheimer-type dementia into contact with test substances;

(n) culturing the nerve cells of Alzheimer-type dementia brought into contact with the test substances in the step (m), and nerve cells of Alzheimer-type dementia not brought into contact with the test substances, as a control, by the method according to [7] or [8]; and (o) measuring Aβ42 and/or Aβ40 in medium of the nerve cells of Alzheimer-type dementia obtained in the step (n), and selecting a test substance for which a content of Aβ42 in the medium of the nerve cells of Alzheimer-type dementia brought into contact with the test substance and/or a value obtained by dividing the content of Aβ42 by a content of Aβ40 therein is lower than that of the control, as a test substance having therapeutic efficacy for Alzheimer-type dementia.

[18] The method according to [17], further includes a step of inducing differentiation into nerve cells of Alzheimer-type dementia from induced pluripotent stem cells produced from somatic cells of a patient with Alzheimer-type dementia or somatic cells of a healthy individual into which a gene mutation causing Alzheimer-type dementia is introduced, and culturing the obtained nerve cells of Alzheimer-type dementia by the method according to [7] or [8], prior to the step (m).

[19] Adherent cells or an adherent cell population is obtained by the methods according to [1] to [8].

[20] In the adherent cells or the adherent cell population according to [19], the adherent cells or the adherent cells are nerve cells.

[21] In the adherent cells or the adherent cell population according to [20], the nerve cells are cells that express one or more marker genes of nerve cells selected from the group consisting of β-III tubulin, NCAM, and MAP2 and that have a neurite.

[22] In the adherent cells or the adherent cell population according to [21], the adherent cells or the adherent cell population contains 50% or more of the cells that express one or more marker genes of nerve cells selected from the group consisting of β-III tubulin, NCAM, and MAP2 and that have a neurite.

[23] In the adherent cells or the adherent cell population according to [20], the nerve cells are cells that express a marker gene of motor nerve cells of HB9 and/or ChAT (choline acetyltransferase) or express one or more marker genes of nerve cells selected from the group consisting of β-III tubulin, NCAM, and MAP2 and that have a neurite and a sufficiently thickened cell body.

[24] In the adherent cells or the adherent cell population according to [23], the adherent cells or the adherent cell population contains 5% or more of the cells that express a marker gene of motor nerve cells of HB9 and/or ChAT (choline acetyltransferase) or express one or more marker genes of nerve cells selected from the group consisting of β-III tubulin, NCAM, and MAP2 and that have a neurite and a sufficiently thickened cell body.

The liquid injection method according to one or more embodiments of the present invention includes: the culture vessel tilting step of tilting the culture vessel around the horizontal axis by a tilt angle X (0°<X≤50°) from the horizontal state; and the liquid injection step of injecting the liquid via the wall surface of the tilted culture vessel at a predetermined linear velocity Y (mm/s) that satisfies the relationship of the formula 1 (Y≤5.075X+123). Thus, cell death specific to adherent cells which are easily detached upon injection of a liquid such as a medium can be assuredly prevented, and operation efficiency can be maximized, while improving the survival rate of the adherent cells, by increasing the linear velocity Y as much as possible within the range of the inequality of the formula 1.

According to one or more embodiments of the culture method for the adherent cells or the adherent cell population of the present invention, living adherent cells can be efficiently collected by using the liquid injection method.

By using the culture method, a growth factor or a nutritional factor useful for culture of adherent cells or an adherent cell population can be efficiently screened, toxicity to adherent cells or an adherent cell population can be efficiently evaluated, and furthermore a substance having therapeutic efficacy for a nervous system disease, a neurodegenerative disease, or Alzheimer-type dementia can be efficiently screened.

DETAILED DESCRIPTION OF THE EMBODIMENTS

Figure 1:
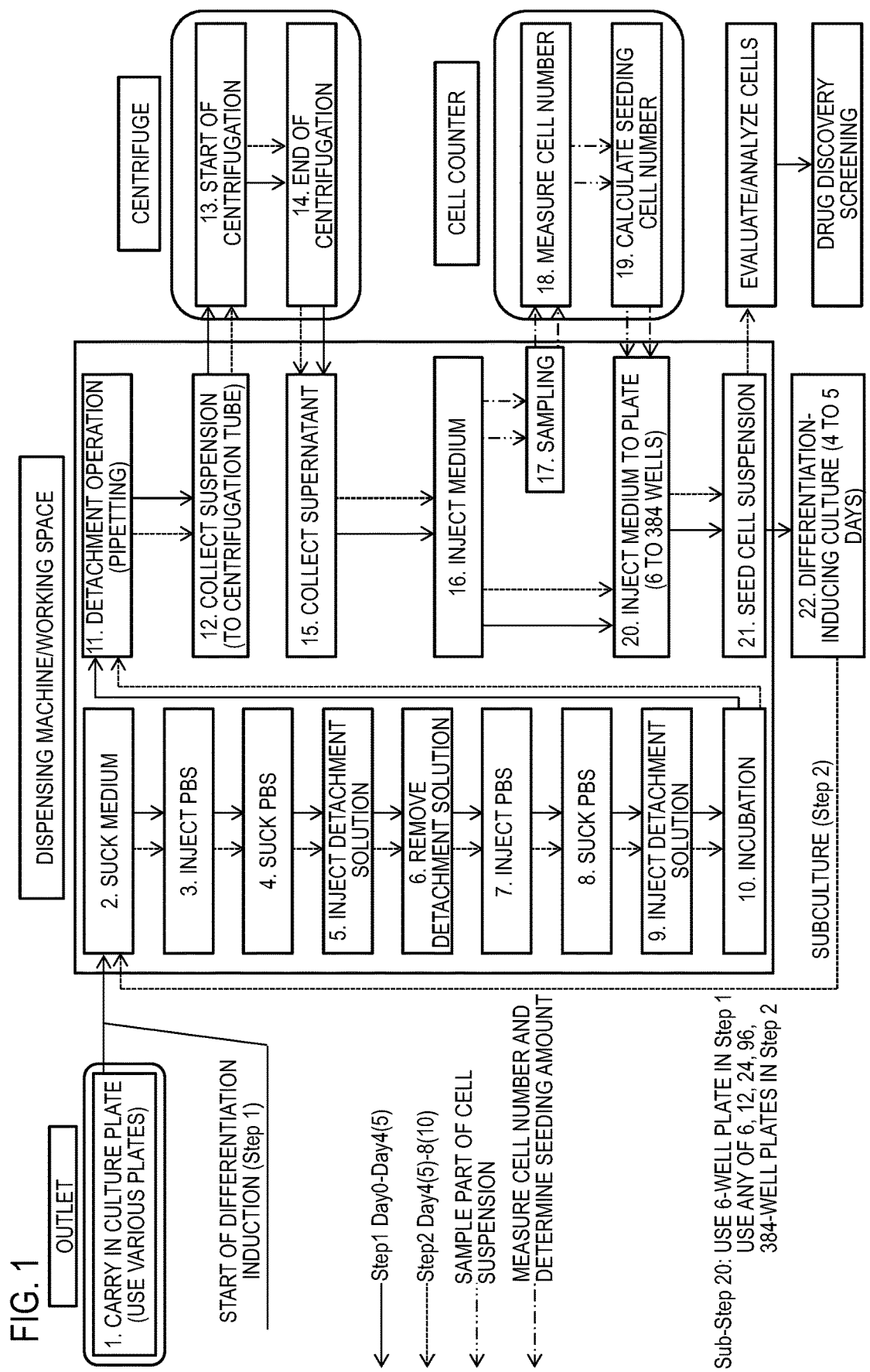
FIG. 1 is a process diagram showing an example of a differentiation-inducing culture method (feeder culture) for iPS cell-derived nerve cells.

Hereinafter, the present invention will be described in detail.

<Liquid Injection Method>

The liquid injection method according to one or more embodiments of the present invention is a method for injecting a required liquid into a culture vessel to which adherent cells or an adherent cell population is adhered, the method including:

a culture vessel tilting step of tilting the culture vessel around a horizontal axis within a range of a tilt angle (X°) of greater than 0° and not greater than 50°, from a state where the culture vessel is horizontal; and a liquid injection step of injecting the liquid at a predetermined linear velocity (Y mm/s) via a wall surface of the culture vessel tilted in the culture vessel tilting step, wherein a relationship between the tilt angle (X) and the linear velocity (Y) satisfies the following (formula 1).

$$Y \leq 5.075X + 123 \quad \text{(formula 1)}$$

Even when a liquid such as a medium is injected into a culture vessel containing adherent cells or an adherent cell population, cell death specific to the adherent cells can be inhibited by one or more embodiments of the present invention. As a result, it becomes possible to maximize operation efficiency while improving the survival rate of the adherent cells.

The adherent cell in the present disclosure refers to a cell having a property of being attached (adhered) to a wall surface of the culture vessel when being cultured within the culture vessel under an appropriate condition. In addition, the term "cell" in the present disclosure includes "a cell population". The adherent cells are defined as an adherent cell population when the adherent cells are present as a cell population due to adhesion or aggregation of multiple adherent cells or when the adherent cells are functionally present as tissues or tissue pieces, and it is obvious to a person skilled in the art that the adherent cells and the adherent cell population are interpreted as having the same meaning. In the present specification, an adherent cell population is sometimes described as a cell population.

The adherent cell is not particularly limited as long as the adherent cell is a cell of which growth or survival depends on stimuli from a cell adhesion molecule on the cell surface, such as a primary cultured cell, stem cell, nerve cell, mesenchymal cell, liver cell, endothelial cell, parietal cell, cardiac muscle cell, and myoblast. Examples of the adherent cell include an induced pluripotent stem (iPS) cell-derived nerve cell, iPS cell-derived motor nerve cell, 293FT cell, primary nerve cell, nerve cell established as a cell line (e.g., human neuroblastoma SH-SY5Y), ReproNeuro (Repro-CELL Incorporated), Human Neuronal Kit (Xcell Science), iCell Nurons (Cellular Dynamics International, Inc.), HEK293 cell, and BHK-21 cell. Among these adherent cells, from the viewpoint of being usable for screening a medicine, iPS cell-derived nerve cell or iPS cell-derived motor nerve cell may be used.

An induced pluripotent stem (iPS) cell-derived nerve cell includes a nerve cell produced by inducing differentiation of an iPS cell.

In addition, the adherent cells or the adherent cell population also includes cell aggregates (i.e., cell sheets) structured as sheet-like tissues by adhering or aggregating the cells. In the cell sheets, for example, the cells may be stratified. The cells can be stratified by, for example, a method disclosed in WO2004/069295, Japanese Unexamined Patent Publication No. 2005-130838, Nishida K et al., N. Engl. J. Med. (2004) 351:1187-96, Nishida K et al., N. Engl. J. Med. (2004) 351:1187-96, Japanese Unexamined Patent Publication No. 2005-130838, WO13/137491, or WO14/192909.

Induced pluripotent stem (iPS) cells are somatic cell-derived artificial stem cells that can be produced by introducing a specific reprogramming factor in the form of DNA or protein into somatic cells and that have properties almost equivalent to those of ES cells, such as pluripotency and proliferation potency via self-replication (K. Takahashi and S. Yamanaka (2006), Cell, 126:663-676; K. Takahashi et al. (2007), Cell, 131:861-872; J. Yu et al. (2007), Science, 318:1917-1920; Nakagawa, M. et al, Nat. Biotechnol. 26:101-106 (2008); International Publication WO2007/069666). Reprogramming factors may be composed of: a gene specifically expressed in ES cells, a gene product thereof, or non-cording RNA; a gene playing an important role in maintenance of undifferentiation of ES cells, a gene product thereof, or non-cording RNA; or a low-molecular-weight compound. Examples of genes contained in such reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3 and Glis1. These reprogramming factors may be used solely or in combination. Examples of a combination of reprogramming factors include those described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO2010/056831, WO2010/068955, WO2010/098419, WO2010/102267, WO2010/111409, WO2010/111422, WO2010/115050, WO2010/124290, WO2010/147395, WO2010/147612, Huangfu D, et al. (2008), Nat. Biotechnol., 26: 795-797, Shi Y, et al. (2008), Cell Stem Cell, 2: 525-528, Eminli S, et al. (2008), Stem Cells. 26:2467-2474, Huangfu D, et al. (2008), Nat Biotechnol. 26:1269-1275, Shi Y, et al. (2008), Cell Stem Cell, 3, 568-574, Zhao Y, et al. (2008), Cell Stem Cell, 3:475-479, Marson A, (2008), Cell Stem Cell, 3, 132-135, Feng B, et al. (2009), Nat Cell Biol. 11:197-203, R. L. Judson et al., (2009), Nat. Biotech., 27:459-461, Lyssiotis C A, et al. (2009), Proc Natl Acad Sci U.S.A. 106:8912-8917, Kim J B, et al. (2009), Nature. 461:649-643, Ichida J K, et al. (2009), Cell Stem Cell. 5:491-503, Heng J C, et al. (2010), Cell Stem Cell. 6:167-74, Han J, et al. (2010), Nature. 463:1096-100, Mali P, et al. (2010), Stem Cells. 28:713-720, and Maekawa M, et al. (2011), Nature. 474: 225-9.

Examples of the above reprogramming factors include histone deacetylase (HDAC) inhibitors [e.g., low-molecular-weight inhibitors such as valproic acid (VPA), trichostatin A, sodium butyrate, MC 1293, and M344, and nucleic acid expression inhibitors such as siRNA and shRNA against HDAC (e.g., HDAC1 siRNA Smartpool (trademark) (Millipore) and HuSH 29mer shRNA Constructs against HDAC1 (OriGene)], MEK inhibitors (e.g., PD184352, PD98059, U0126, SL327, and PD0325901), Glycogen synthase kinase-3 inhibitors (e.g., Bio and CHIR99021), DNA methyltransferase inhibitors (e.g., 5-azacytidine), histone methyltransferase inhibitors (e.g., low-molecular-weight inhibitors such as BIX-01294, and nucleic acid expression inhibitors such as siRNA and shRNA against Suv39h1, Suv39h2, SetDB1 and G9a), L-channel calcium agonists (e.g., Bayk8644), butyric acid, TGFβ inhibitors or ALK5 inhibitors (e.g., LY364947, SB431542, 616453, and A-83-01), p53 inhibitors (e.g., siRNA and shRNA against p53), ARID3A inhibitors (e.g., siRNA and shRNA against ARID3A), miRNAs such as miR-291-3p, miR-294, miR-295, and mir-302, Wnt Signaling (e.g., soluble Wnt3a), neuropeptide Y, prostaglandins (e.g., prostaglandin E2 and prostaglandin J2), and factors to be used for enhancing the efficiency of establishment, such as hTERT, SV40LT, UTF1, IRX6, GLIS1, PITX2, and DMRTB1. In the present specification, these factors used for improving the efficiency of establishment are not particularly distinguished from the reprogramming factors.

Reprogramming factors in the form of protein may be introduced into somatic cells by a technique such as lipofection, fusion with a cell membrane-permeable peptide (e.g., HIV-derived TAT and polyarginine), or microinjection.

Meanwhile, reprogramming factors in the form of DNA can be introduced into somatic cells by a technique such as a technique using a vector such as a virus, a plasmid, or an artificial chromosome, lipofection, a technique using a liposome, or microinjection. Examples of viral vectors include a retrovirus vector, a lentivirus vector (disclosed for these in Cell, 126, pp. 663-676, 2006; Cell, 131, pp. 861-872, 2007; and Science, 318, pp. 1917-1920, 2007), an adenovirus vector (Science, 322, 945-949, 2008), an adeno-associated virus vector, and a Sendai virus vector (WO2010/008054). Also, examples of artificial chromosome vectors include a human artificial chromosome (HAC), a yeast artificial chromosome (YAC), and a bacterial artificial chromosome (BAC, PAC). As a plasmid, a plasmid for mammalian cells can be used (Science, 322: 949-953, 2008). A vector can contain regulatory sequences such as a promoter, an enhancer, a ribosome binding sequence, a terminator, and a polyadenylation site, so that a nuclear reprogramming substance can be expressed. The vector may further contain, as necessary, a drug resistance gene (e.g., a kanamycin resistance gene, an ampicillin resistance gene, and a puromycin resistance gene), a selection marker sequence such as a thymidine kinase gene and a diphtheria toxin gene, and a reporter gene sequence such as a green fluorescent protein (GFP), β glucuronidase (GUS), and FLAG. Moreover, the above vector may contain LoxP sequences before or behind a gene encoding a reprogramming factor, or a gene encoding a promoter and a reprogramming factor binding to the promoter, so as to excise the gene or both the gene after introduction of the vector into somatic cells.

Furthermore, reprogramming factors in the form of RNA may be introduced into somatic cells by a technique such as lipofection or microinjection. For suppression of degradation, RNA into which 5-methylcytidine and pseudouridine (TriLink Biotechnologies) are incorporated may be used (Warren L, (2010) Cell Stem Cell. 7:618-630).

In the following description, in order to distinguished nerve cells induced by introducing a nerve cell-inducing factor into iPS cells, or motor nerve cells induced by introducing a motor nerve cell-inducing factor into iPS cells, from nerve cells or motor nerve cells obtained by another method, such nerve cells and such motor nerve cells are sometimes referred to as induced neurons (iN) and induced motor neurons (iMN), respectively. Here, motor nerve cell-inducing factors (MN-inducing factors) are suitably Lhx3, Ngn2, and Isl1 genes, and a nerve cell-inducing factor (or N-inducing factors) is suitably only Ngn2 gene.

<Nerve Cells (iN)>

A nerve cell is defined as a cell that expresses one or more of marker genes for nerve cells, such as β-III tubulin, NCAM, and MAP2, and that has a neurite. Accordingly, the criteria for determining iN complies with this definition. Furthermore, the nerve cell may be glutamatergic. Even when nerve cells are described in the present disclosure, the nerve cells are not necessarily limited to a uniform cell population, but mean that a cell population containing cells that satisfy the above definition is obtained, and may be a cell population containing not less than 50%, 60%, 70%, 80%, 90%, 95%, 98%, or 99% of cells that satisfy the definition.

Since Tuj1 is an anti-β-III tubulin, a cell expressing the β-III tubulin is sometimes referred to as Tuj1-positive cell.

<Motor Nerve Cells (iMN)>

A motor nerve cell is defined as a cell that expresses one or more of marker genes for motor nerve cells, such as HB9 and ChAT (choline acetyltransferase), or a cell that expresses one or more of marker genes for nerve cells, such as β-III tubulin, NCAM, and MAP2, and that has a neurite and a sufficiently thickened cell body. This is because it has been confirmed that expression of HB9 or ChAT is observed in a cell that expresses one or more of the marker genes for nerve cells and that has a neurite and a sufficiently thickened cell body. Accordingly, the criteria for determining iMN complies with this definition. Even when motor nerve cells are described in the present disclosure, the motor nerve cells are not necessarily limited to a uniform cell population, but mean that a cell population containing cells that satisfy the above definition is obtained, and may be a cell population containing not less than 5%, 15%, 20%, 30%, 40%, 50%, 60%, 70%, 80%, 90%, or 95% of cells that satisfy the definition.

The above induced pluripotent stem cells may be produced from somatic cells of a patient with a nervous system disease or somatic cells of a healthy individual into which a gene mutation causing the nervous system disease is introduced.

In one or more embodiments of the present invention, a person diagnosed as not developing a pathological condition associated with the nervous system disease is referred to as healthy individual.

In one or more embodiments of the present invention, the nervous system disease refers to a disease caused by denaturation or deletion of nerve cells, and examples of nervous system diseases include Alzheimer-type dementia, Parkinson's disease, Lewy body dementia, amyotrophic lateral sclerosis (ALS), Huntington's disease, and spinocerebellar degeneration.

In one or more embodiments of the present invention, the culture vessel may be any vessel as long as the vessel allows culture of the adherent cells or the adherent cell population, and examples of the culture vessel include a multi-well plate, a microplate, a micro-well plate, a multi-dish, a dish, and a flask for tissue culture. Examples of the microplate include a 6-well plate, a 12-well plate, a 24-well plate, a 96-well plate, and a 384-well plate, and examples of the dish include a 35-mm dish, a 60-mm dish, and a 100-mm dish.

Examples of the material of the culture vessels include polystyrene, polypropylene, and polyethylene, and polystyrene may be used since polystyrene has excellent transparency required for cell observation.

Each culture vessel has a vessel portion including a bottom portion and a wall surface connected to the bottom portion, and culture of adherent cells can be carried out by introducing a culture solution containing adherent cells or an adherent cell population into the vessel portion and adjusting culture conditions such as temperature and time to appropriate conditions. The material of the culture vessel is not particularly limited, and a culture vessel subjected to surface treatment for improving adhesion of cells is desired. Such a culture vessel subjected to surface treatment is available from Corning Incorporated, Sumitomo Bakelite Co., Ltd., or AGC TECHNO GLASS Co., Ltd. In addition to the above, a coating agent such as an extracellular matrix protein may be used for enhancing the adhesiveness of cells, and examples of extracellular matrix proteins include collagen, gelatin, laminin, heparan sulfate proteoglycan, entactin, fragments or mixtures thereof, and synthetic substrates such as poly-L-lysine, Synthemax (Corning Incorporated), and Synthemax-II (Corning Incorporated).

In the case of producing a cell sheet as the adherent cells or the adherent cell population, an appropriate vessel for cell sheet production may be used depending on the type of the cells.

The shape, the size, and the like of the culture vessel are not particularly limited.

In one or more embodiments of the present invention, the culture vessel to which the adherent cells or the adherent cell population are adhered refers to a culture vessel in a state where the adherent cells or the adherent cell population is adhered to the surface of the vessel portion of the culture vessel, particularly, to the bottom surface of the vessel portion.

The state where the adherent cells or the adherent cell population is adhered to the culture vessel only needs to be, for example, a state where at least part of the adherent cells or the adherent cell population is adhered to the surface of the vessel portion of the culture vessel by introducing a culture solution containing the adherent cells or the adherent cell population into the culture vessel and carrying out culture at a predetermined temperature for a predetermined time.

In one or more embodiments of the present invention, the state where the culture vessel is horizontal refers to a state where the culture vessel is disposed parallel to a plane perpendicular to the gravity direction (a horizontal plane).

In one or more embodiments of the present invention, from the viewpoint of easily performing an injection operation, the outer surface of the bottom portion of the culture vessel is formed so as to be parallel to the horizontal plane and the wall surface of the culture vessel is formed so as to extend in a direction substantially perpendicular to the horizontal plane.

In one or more embodiments of the present invention, the horizontal axis refers to a coordinate axis extending in a lateral direction of the horizontal plane that is in contact with the outer surface of the bottom portion of the culture vessel in a state where the culture vessel is horizontal.

In one or more embodiments of the present invention, the horizontal axis for the culture vessel is determined in any of the right and left directions of the horizontal plane, and the culture vessel is tilted in a rotational direction around the horizontal axis.

In addition, "around the horizontal axis" means any of rotational directions about the horizontal axis.

In one or more embodiments of the present invention, the tilt angle refers to an angle relative to the horizontal axis when the culture vessel is tilted from a state where the culture vessel is horizontal.

In one or more embodiments of the present invention, the linear velocity of the liquid refers to a velocity at which the liquid passes through the cross-section of the tip end of a pipette tip per unit time, and is indicated in unit (mm/s).

The linear velocity can be calculated by measuring the velocity at which the liquid passes through the cross-section of the tip end of the pipette tip per unit time, with a flow meter, and dividing the velocity by the cross-sectional area of the pipette tip.

In one or more embodiments of the present invention, the required liquid is not particularly limited as long as the required liquid is a liquid exhibiting fluidity, and examples of the required liquid include fluid materials such as a saline, a buffer, a medium, and a washing solution.

As the medium, a basal medium may be used, and the medium having additives added thereto can be used.

The basal medium is not particularly limited as long as the basal medium is a medium that can be used for culture of animal cells, such as Neurobasal medium, Neural Progenitor Basal medium, NS-A medium, BME medium, BGJb medium, CMRL 1066 medium, Glasgow MEM medium, Improved MEM Zinc Option medium, IMDM medium, Medium 199 medium, Eagle MEM medium, αMEM medium, DMEM medium, DMEM/F12 medium, Ham's medium, RPMI 1640 medium, Fischer's medium, and mixed media thereof. In the case of culturing iN or iMN, a mixture of Neurobasal medium and DMEM/F12 is suitably used.

The additives are not particularly limited, and examples of the additives include substances required for growth or survival of cells, such as serum, retinoic acid, Wnt, BMP, bFGF, EGF, HGF, Sonic hedgehog (Shh), neurotrophic factor family, insulin-like growth factor 1 (IGF1), amino acids, vitamins, interleukins, insulin, transferrin, heparin, heparan sulfate, collagen, fibronectin, progesterone, selenite, B27-supplement, N2-supplement, ITS-supplement, and antibiotics. In the case of culturing iN or iMN, retinoic acid, Shh, BDNF, GDNF, NT-3, B27-supplement, and N2-supplement are suitably used. The neurotrophic factor family may be Brain-derived Neurotrophic Factor (BDNF), Glial cell line-derived Neurotrophic Factor (GDNF), and Neurotrophin 3 (NT-3). These additives may be added at one time, or may be changed stepwise in accordance with elapse of culture. In the case of culturing iN or iMN, a step of carrying out culture in a medium to which BDNF, GDNF, NT-3, B27-supplement, and N2-supplement are added, after culture in a medium to which retinoic acid, Shh, B27-supplement, and N2-supplement are added, is exemplified.

The washing solution is not particularly limited as long as only contaminants and cells to be removed can be washed away by the washing solution, and examples of the washing solution include a saline, a Ringer's solution, a medium to be used for cell culture, a general buffer such as a phosphate buffer, or solutions obtained by adding serum or a protein to these solutions.

Next, each step of the liquid injection method according to one or more embodiments of the present invention will be specifically described.

(Culture Vessel Tilting Step)

In this step, the culture vessel to which the adherent cells or the adherent cell population is adhered is tilted around the horizontal axis within a range of a predetermined tilt angle X ($0°<X≤50°$) from a state where the culture vessel is horizontal.

The tilt angle (X) is not unconditionally specified depending on the type of the culture vessel, the linear velocity at which the liquid is to be injected, and the like, but is set as $X≤50°$ for preventing overflowing of the injected liquid from the culture vessel as much as possible. Thus, the range of the tilt angle X is $0°<X≤50°$. In addition, in order to assuredly prevent overflowing of the injected liquid, the tilt angle (X) may be set as $X≤40°$. Furthermore, the tilt angle X (°) may be set to be greater than 30°, since cell death is rapidly reduced.

Therefore, in order to prevent overflowing of the injected liquid and in order to increase the operation efficiency as much as possible while improving the survival rate of the cells, the tilt angle X may be set within the range of not less than 30° and not greater than 40° (that is, $30°≤X≤40°$. It is possible to substitute the value of the tilt angle X as a result of tilting in this manner into the inequality of the above formula 1 and to set the linear velocity Y to be as high as possible within the range of the inequality of the formula 1. The range of the tilt angle X is not particularly limited as long as the range is $0°<X≤50°$, and the range of the tilt angle X may be set as $30°≤X≤40°$ as described above, but may be not less than 5° ($X≥5°$), may be not less than 10° ($X≥10°$), or may be not less than 20° ($X≥20°$).

An operation of tilting the culture vessel around the horizontal axis from the state where the culture vessel is horizontal in this step, and an operation of returning the culture vessel to a horizontal state may be performed by manually rotating a table supporting the culture vessel around the horizontal axis, or may be performed electrically by using a stepping motor or a servomotor.

Figure 3:
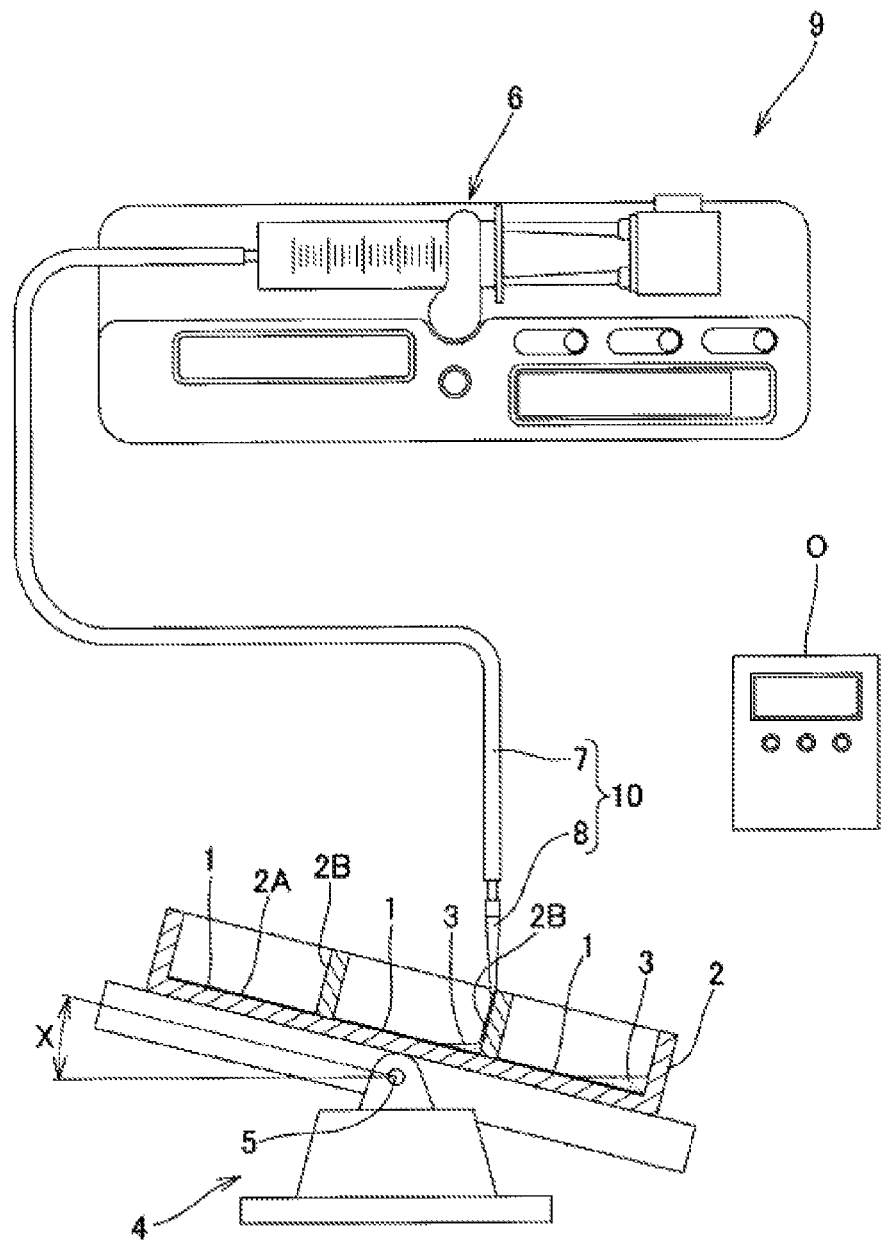
FIG. 3 is a partially cross-sectional schematic diagram showing an apparatus for an experiment carried out for establishing the liquid injection method according to one or more embodiments of the present invention.

For example, a multi-well plate 2 that is a culture vessel shown in FIG. 3 is fixed to a tilting table 4 in a state where the multi-well plate 2 is placed on the tilting table 4. The tilting table 4 is configured to be able to hold the multi-well plate 2 in a horizontal state and in a state where the multi-well plate 2 is tilted around a horizontal support axis 5 by the tilt angle X (°) from the horizontal state.

(Liquid Injection Step)

In this step, the liquid is injected at a predetermined linear velocity (Y mm/s) via the wall surface of the culture vessel tilted in the culture vessel tilting step.

In this step, since the liquid is injected via the wall surface of the culture vessel, influence on the adherent cells such as impact can be minimized as compared to the case where the liquid is dropped directly to the adherent cells or the adherent cell population attached to the bottom surface within the culture vessel.

As means for injecting the liquid, appropriate injecting means may be used in accordance with the shape and the size of the culture vessel, and examples of the injecting means include a pipette, a micropipette, a syringe, a dispensing device, and a culture device. Examples of the dispensing device include "Biomek" manufactured by Beckman Coulter, Inc., "Freedom EVO" manufactured by Tecan Trading AG, and "MICROLAB" manufactured by Hamilton Company.

Examples of an apparatus for executing the liquid injection method include, in addition to a simple apparatus including a tilting table for tilting a plate and a syringe pump for feeding a liquid as shown in FIG. 3, an automatic culture system that is optimum for cell culture and includes: a dispensing machine for dispensing a liquid; an incubator for culturing cells; a centrifuge for collecting cells; a cell counter for measuring a cell number; a cooling box for cooling reagents; a heater for heating a medium; a transfer arm for transferring a culture vessel; and a barcode reader for managing a culture vessel. Specific examples of the automatic culture system include commercially available "Cell Farm" manufactured by Kiko Tech Co., Ltd. and "AUTO CULTURE" manufactured by Kawasaki Heavy Industries, Ltd.

For example, as shown in FIG. 3, the tip end of a pipette tip 8 is located above a wall surface 2B at the lower side of a well of the multi-well plate 2 that is tilted by the tilting table 4.

Next, a liquid 3 is injected into the multi-well plate 2 from a syringe pump 6 via a pipe 7 with the pipette tip 8.

The injection of the liquid 3 out of the pipette tip 8 is performed until the liquid 8 reaches nerve cells 1 attached to a bottom surface 2A, via the wall surface 2B of the multi-well plate 2.

In addition, in a state where the tip end of the pipette tip 8 is located in, for example, a ½ lower side region, a ⅓ lower side region, a ¼ lower side region, a ⅕ lower side region, or a lowermost region of the inner wall (2B in FIG. 3), to which the adherent cells or the adherent cell population is not attached, of a wall erected from the bottom surface (2A in FIG. 3) having the adherent cells or the adherent cell population attached thereto, a required liquid is injected into the culture vessel that is tilted through the culture vessel tilting step, at a predetermined linear velocity Y from the pipette tip via the inner surface of the wall.

This step is prominently characterized by injecting the liquid such that the relationship between the tilt angle (X) of the culture vessel and the linear velocity (Y) of the liquid satisfies the following (formula 1).

$$Y \leq 5.075X + 123 \quad \text{(formula 1)}$$

Since the tilt angle (X) of the culture vessel and the linear velocity (Y) of the liquid are adjusted so as to satisfy the formula 1 as described above, even when a liquid such as a medium is injected into the culture vessel containing adherent cells or an adherent cell population, cell death specific to the adherent cells can be inhibited. As a result, it becomes possible to maximize the operation efficiency while improving the survival rate of the adherent cells.

The formula 1 is experientially found out for the first time by the present inventors focusing on the tilt angle (X) of the culture vessel and the linear velocity (Y) of the liquid, and repeating an injection experiment using various adherent cells or adherent cell populations for the purpose of inhibiting cell death. The highest velocity (=5.075X+123) can be predicted as the linear velocity (Y) at which the liquid is injected in this step, on the basis of the tilt angle (X) by which the culture vessel is tilted in the culture vessel tilting step.

When the linear velocity (Y) measured by using the formula (1) is adjusted as $Y < 5.075X + 123$, it becomes possible to further inhibit cell death of the adherent cells or the adherent cell population.

An automated apparatus that can suitably execute the liquid injection method according to one or more embodiments of the present invention will be described with reference to FIG. 3.

The automated apparatus 9 includes the tilting table 4 on which a culture vessel 2 can be set, and a pipetter 10 for sucking a liquid within the culture vessel 2 or feeding a liquid into the culture vessel 2. The pipetter 10 attachably and detachably includes the pipette tip 8 for sucking a liquid, and the pipetter 10 is configured such that the position of the pipette tip 8 is movable vertically and horizontally.

The automated apparatus 9 is provided with a control unit O that controls the position of the pipetter 10 and tilt of the tilting table 4. The control unit O is composed of a CPU or the like.

As control of the tilting table 4 and the pipetter 10 by the control unit O, specifically, the control unit O controls motion such that: the pipetter 10 is moved to above the culture vessel 2 that is set on the tilting table 4; the tilting table 4 is tilted such that the relationship between the tilt angle (X) of the tilting table 4 and the linear velocity (Y) at which a liquid is injected from the pipetter 10 satisfies $Y \leq 5.075X + 123$ when the pipette tip 8 is inserted into the culture vessel 2 and the liquid is injected; and the liquid sucked by the pipetter 10 is discharged therefrom. In another embodiment, the control unit O controls motion such that: the tilting table 4 is tilted prior to movement of the pipetter 10; then the pipetter 10 is moved to above the culture vessel 2 that is set on the tilting table 4; the pipette tip 8 is inserted into the culture vessel 2; and the liquid sucked by the pipetter 10 is discharged therefrom. At this time, the relationship between the tilt angle (X) of the tilting table 4 and the linear velocity (Y) at which the liquid is injected from the pipetter 10 is controlled by the control unit O so as to satisfy $Y \leq 5.075X + 123$. After end of the injection of the liquid or after oscillation, control may be performed by the control unit O so as to return the tilting table 4 to a horizontal state. In addition, control may be performed by the control unit O so as to detach the pipette tip 8 from the pipetter 10.

In the case where the culture vessel 2 has a plurality of wells, the control unit O may control motion such that the pipetter 10 is moved away from a well on which liquid injection has been finished, the pipette tip 8 of the pipetter 10 is inserted into another well, and the liquid is injected thereinto. In the case where a plurality of the culture vessels 2 are present, similarly to the case where a plurality of wells are present, the control unit O may control motion such that the pipetter 10 is moved away from the inside of a culture vessel on which liquid injection has been finished, the pipette tip 8 of the pipetter 10 is inserted into another culture vessel, and the liquid is injected thereinto. In the case where the cell strains of the adherent cells or the adherent cell population within the respective culture vessels are different from each other, in order to prevent contamination of cells between the culture vessels, the control unit O may control motion such that each time liquid injection into one culture vessel is finished, the pipette tip is detached from the pipetter 10 and replaced with a new pipette tip.

The control unit O may perform control such that in transferring the liquid into the culture vessel 2, the liquid to be transferred to the pipette tip 8 is sucked and then air is sucked thereby to form an air layer at the tip end of the pipette tip 8, then the pipette tip 8 is moved to the transfer destination of the liquid, and the liquid sucked by the pipette tip 8 is discharged, whereby liquid dripping is prevented in transferring the liquid. In addition, the control unit O may perform control such that in discharging the liquid sucked by the pipette tip 8, movement of the pipette tip 8 is stopped for a predetermined standby time from start of discharge of the liquid sucked by the pipette tip 8, and the standby time is lengthened in accordance with the amount of the liquid to be discharged by the pipette tip 8.

The liquid injection method according to one or more embodiments of the present invention including the above steps is suitably used for various methods using culture vessels, for example, a method for culturing adherent cells or an adherent cell population, a method for screening a growth factor or a nutritional factor useful for culture of adherent cells or an adherent cell population, a method for evaluating toxicity to adherent cells or an adherent cell population, and a method for screening a substance having therapeutic efficacy for a nervous system disease, a neurodegenerative disease, or Alzheimer-type dementia. Hereinafter, these methods will be described in detail.

<Method for Culturing Adherent Cells or Adherent Cell Population within Culture Vessel>

The method for culturing adherent cells or an adherent cell population within a culture vessel (hereinafter, culture method for the adherent cells or the adherent cell population) according to one or more embodiments of the present invention includes a step of sucking a medium within the culture vessel, injecting a fresh medium into the culture vessel, and culturing the adherent cells or the adherent cell population, and the above liquid injection method is used for injecting the fresh medium.

In the culture method for the adherent cells or the adherent cell population according to one or more embodiments of the present invention, cell death of the adherent cells or the adherent cell population due to liquid injection can be inhibited by using the above liquid injection method in injecting the medium. Thus, the adherent cells or the adherent cell population can be efficiently cultured. Before the liquid is injected, the medium may be fully removed or may be partially removed. In addition, as the medium to be injected, a fresh medium having the same composition as that of the removed medium, a medium having a composition different from that of the removed medium, or a medium obtained by adding a new compound or the like to each medium can be used.

The culture method for the adherent cells or the adherent cell population according to one or more embodiments of the present invention may include a step (cell seeding step) of seeding the adherent cells or the adherent cell population into the culture vessel, or a step (culture step) of culturing a culture solution containing the adherent cells or the adherent cell population at a predetermined temperature for a predetermined time, etc. The operation of the liquid injection can be performed as appropriate when the culture step is continuously performed.

The culture step also includes a step of increasing a cell number and a step of inducing differentiation of cells having differentiation potency. In addition, the culture step also includes a step of carrying out maintenance culture in which the cell number is not increased.

As the medium used in the culture method for the adherent cells or the adherent cell population according to one or more embodiments of the present invention, the above-described media can be used as appropriate.

The culture method for the adherent cells or the adherent cell population according to one or more embodiments of the present invention may also include a washing step of washing the interior of the culture vessel by injecting a washing solution into the culture vessel and sucking the washing solution. Cell death of the adherent cells or the adherent cell population due to the injection of the washing solution can be inhibited by using the above liquid injection method also for injecting the washing solution. Thus, the adherent cells or the adherent cell population can be safely washed.

The washing step may be performed after the culture step or during the culture. The washing step can be performed when cells are subcultured, before the medium is removed and treatment is performed with a detachment solution, when the surface of the culture vessel to which the cells are attached is washed, or when the washing solution is injected.

For the purpose of subculturing the adherent cells or the adherent cell population, the culture method for the adherent cells or the adherent cell population according to one or more embodiments of the present invention may further include:

a cell detachment step of injecting a detachment solution to the adherent cells or the adherent cell population within the culture vessel;

a centrifugation step of transferring the cell suspension obtained in the cell detachment step to a centrifugation tube and performing centrifugation with a centrifuge;

a resuspension step of removing the supernatant within the centrifugation tube having undergone the centrifugation step, and injecting a medium into the centrifugation tube;

a cell number measurement and cell concentration adjustment step of sampling a part of the cell suspension obtained by the resuspension step, measuring a cell number, and adjusting the cell concentration of the cell suspension on the basis of a result of the measurement in order to seed cells; and a cell seeding step of seeding the cells having a required cell number adjusted in the cell number measurement and cell seeding amount adjustment step, into a culture vessel filled with a medium.

The detachment solution in one or more embodiments of the present invention may be any solution as long as the solution can safely detach the adherent cells or the adherent cell population adhered within the culture vessel. Examples of the detachment solution include a solution containing an enzyme such as trypsin. From the viewpoint that the adherent cells or the adherent cell population can be safely collected by injecting the detachment solution, a CTK solution (a PBS solution obtained by adding 0.25% of trypsin, 1 mg/mL of collagenase, 1 mM of $CaCl_2$, and 20% of KSR) may be used.

Detachment means other than the detachment solution in the cell detachment step may be any means as long as the means is based on a publicly known method, and the detachment means is not particularly limited.

The cell detachment step may be performed after the culture step or after the washing step.

The centrifugation tube and the centrifuge used in the centrifugation step may be any tube and any centrifuge as long as the centrifugation tube and the centrifuge are publicly known ones, and the centrifugation tube and the centrifuge are not particularly limited.

The cell number measurement and cell concentration adjustment step is a step of measuring the number of the adherent cells or the adherent cell population per unit quantity of the cell suspension by sampling a part of the cell suspension obtained in the resuspension step, calculating the concentration of the cell suspension, and adjusting the cell concentration of the cell suspension and/or adjusting an amount of the cell suspension to be seeded, on the basis of this concentration in order to seed the cell suspension at an appropriate density into a fresh culture vessel.

The method for removing the supernatant or sampling a part of the resuspended cell suspension may be any method as long as the method is based on a publicly known method, and the method is not particularly limited.

As the method for measuring a cell number, a cell number can be measured with a counter while observation is performed with a microscope using a counting chamber, or a cell number can be measured by using a cell counter.

In the case of measuring the cell number of nerve cells, the measurement may be performed by the following method.

(Cell Number Measurement of Nerve Cells)

The number of the nerve cells in the cell suspension can be measured as the number of cells expressing a nerve cell marker gene such as β-tubulin by performing immunostaining using a method known to a person skilled in the art. For example, the number of the nerve cells in the cell suspension may be automatically measured by using a cell image analyzer ("IN Cell Analyzer" manufactured by GE Healthcare Science, "CellInsight" manufactured by Thermo Fisher Scientific, Inc.).

In the cell seeding step performed next, a required volume of the cell suspension adjusted in the cell number measurement and cell concentration adjustment step is seeded into a culture vessel filled with a medium.

<Method for Screening Growth Factor or Nutritional Factor Useful for Culture of Adherent Cells>

The method for screening a growth factor or a nutritional factor useful for culture of adherent cells or an adherent cell population according to one or more embodiments of the present invention includes the following steps (a) to (c):

(a) a step of bringing adherent cells or an adherent cell population into contact with test substances;

(b) a step of culturing the adherent cells or the adherent cell population brought into contact with the test substances by the step (a), and adherent cells or adherent cell population not brought into contact with the test substances, as a control, by the culture method for the adherent cells or the adherent cell population; and (c) a step of measuring the cell number of the adherent cells or the adherent cell population obtained in the step (b) and selecting a test substance for which the cell number of the adherent cells or the adherent cell population brought into contact with the test substance is higher than that of the control, as a growth factor or a nutritional factor useful for culture of the adherent cells or the adherent cell population.

In the method for screening a test substance that is a growth factor or a nutritional factor useful for culture of adherent cells or an adherent cell population according to one or more embodiments of the present invention, in the step (b), since the adherent cells or the adherent cell population brought into contact with the test substances or not brought into contact with the test substances are cultured by using the culture method for the adherent cells or the adherent cell population, even when the culture is continuously carried out, cell death of the adherent cells or the adherent cell population due to replacement of the medium can be inhibited. In addition, presence or absence of action as a growth factor or a nutritional factor on the test substances can be confirmed by comparing the results of culture of the two types of the adherent cells or the adherent cell population.

In one or more embodiments of the present invention, the test substances that are used in each screening (screening of a growth factor or a nutritional factor, screening for adherent cells, screening of a substance having therapeutic efficacy for a nervous system disease, screening of a substance having therapeutic efficacy for a neurodegenerative disease due to protein misfolding, and screening of a substance having therapeutic efficacy for Alzheimer-type dementia) and brought into contact with cells are not particularly limited. Examples of usable test substances include, but are not limited thereto, cell extracts, nucleic acids (DNA, RNA, PNA), expression products of gene libraries, synthetic low-molecular-weight compounds, synthetic peptides, natural compound, serum, plant extracts, fruits extracts, retinoic acid, Wnt, BMP, bFGF, EGF, HGF, Sonic hedgehog (Shh), Brain-derived Neurotrophic Factor (BDNF), Glial cell line-derived Neurotrophic Factor (GDNF), Neurotrophin 3 (NT-3), insulin-like growth factor 1 (IGF1), amino acids, vitamins, interleukins, insulin, transferrin, heparin, heparan sulfate, collagen, fibronectin, progesterone, selenite, B27-supplement, N2-supplement, and ITS-supplement. Retinoic acid, Shh, BDNF, GDNF, NT-3, B27-supplement, N2-supplement, Vincristine (Sigma-Aldrich), Paclitaxel (Sigma-Aldrich), Colchicine (Tokyo Chemical Industry Co., Ltd.), Docetaxel (Fluka), Doxorubicin (Wako Pure Chemical Industries, Ltd.), Vindesine (Sigma-Aldrich), and Vinorelbine (Sigma-Aldrich) can be used.

Examples of the growth factor useful for culture of adherent cells or an adherent cell population in one or more embodiments of the present invention include BDNF, FGFb, Activin A, and EGF as general growth factors, and also include cytokines.

Examples of the nutritional factors useful for culture of adherent cells or an adherent cell population in one or more embodiments of the present invention include nutrients such as amino acids, sugar, lipid, and vitamins.

In one or more embodiments of the present invention, nerve cells may be used as the adherent cells or the adherent cell population. When nerve cells are used, growth factors or nutritional factors that are the test substances may be limited to neurotrophic factors, and examples of the neurotrophic factors include Nerve Growth Factor (NGF), Brain-derived Neurotrophic Factor (BDNF), Neurotrophin 3 (NT-3), Neurotrophin 4/5 (NT-4/5), Neurotrophin 6 (NT-6), basic FGF, acidic FGF, FGF-5, Epidermal Growth Factor (FGF), Hepatocyte Growth Factor (HGF), Insulin, Insulin like Growth Factor 1 (IGF 1), Insulin like Growth Factor (IGF 2), Glial cell line-derived Neurotrophic Factor (GDNF), TGF-b2, TGF-b3, Interleukin 6 (IL-6), Ciliary Neurotrophic Factor (CNTF), and LIF.

Examples of the method for bringing the adherent cells or the adherent cell population into contact with each test substance in the step (a) include, but are not particularly limited thereto, a method in which the test substance is mixed into a medium containing the adherent cells or the adherent cell population, and a method in which a medium is replaced with a medium in which the test substance is added in advance.

As the method for culturing the adherent cells or the adherent cell population in the step (b), the adherent cells or the adherent cell population may be cultured according to the above culture method for the adherent cells.

In the step (c), as the method for measuring the cell number of the adherent cells or the adherent cell population obtained in the step (b), a part of the medium containing the adherent cells or the adherent cell population may be sampled, and the number of the cells contained therein may be measured in the same manner as described above, or may be calculated as the opposite of the number of dead cells. Measurement of the number of dead cells can be performed by, for example, a method for measuring the activity of LDH, a method for measuring absorbance using MTT method, WST-1 method, or WST-8 method, or a method in which dead cells are strained with TO (thiazole orange), PI (propidium iodide), 7AAD, calcein-AM, or an ethidium homodimer (EthD-1) and counted with a flow cytometer, and further can be automatically performed with a cell image analyzer.

If there is a test substance for which the cell number of the adherent cells or the adherent cell population brought into contact with the test substance is higher than that of the control, this test substance can be determined as a growth factor or a nutritional factor useful for culture of the adherent cells or the adherent cell population.

Instead of the adherent cells or the adherent cell population not brought into contact with the test substances as the control cells in one or more embodiments of the present invention, cells brought into contact with a drug confirmed as not having efficacy can be used.

<Method for Evaluating Toxicity of Test Substance to Adherent Cells or Adherent Cell Population>

The method for evaluating toxicity to adherent cells or an adherent cell population according to one or more embodiments of the present invention includes the following steps (d) to (f):

(d) a step of bringing adherent cells or an adherent cell population to test substances;

(e) a step of culturing the adherent cells or the adherent cell population brought into contact with the test substances in the step (d), and adherent cells or an adherent cell population not brought into contact with the test substances, as a control, by the above culture method for the adherent cells or the adherent cell population; and (f) a step of measuring the cell numbers of the adherent cells obtained in the step (e) and evaluating the test substance for which the cell number of the adherent cells brought into contact with the test substance is lower than that of the control, as having toxicity to the adherent cells or the adherent cell population.

In the method for evaluating toxicity to the adherent cells or the adherent cell population according to one or more embodiments of the present invention, in the step (e), since the adherent cells or the adherent cell population brought into contact with the test substances and the adherent cells or the adherent cell population not brought into contact with the test substances are cultured by using the above culture method for the adherent cells or the adherent cell population, cell death of the adherent cells or the adherent cell population due to liquid injection upon medium replacement, washing, or the like can be inhibited. Thus, the toxicity of each test substance can be accurately confirmed without influence of a decrease in the adherent cells or the adherent cell population that is not involved in toxicity of the test substance.

The toxicity in the present disclosure means that when a test substance is brought into contact with culture cells, life and death of the cells, that is, the survival rate (or death rate) of the cells increases, and change of the length (shortening, disappearance, etc.) of neurite occurs in the case of nerve cells.

Examples of the evaluating method include a method in which a cell number is directly measured, a method in which colonies produced from multipliable cells are counted, and a method in which a specific substance is quantitated by an optical method or with a radiolabeled compound and a survival rate and a death rate is indirectly estimated.

For measuring cell death, presence or absence of destruction of a cell membrane is most frequently used. A dye such as trypan blue does not enter living cells, but enter dead cells to stain the dead cells. Accordingly, the living/dead cells are counted under a microscope. In addition, a substance leaking from the cytoplasm of dead cells may be used, and a typical method is a method in which the activity of a lactate dehydrogenase (LDH) is measured.

Next, there is a method using a function of living cells or a substance in living cells. As a method using the reducing power of living cells, there is MTT assay in which a tetrazolium salt such as MTT is incorporated into living cells and is reduced to be formazan which colors the living cells. In addition to this method, there is a method using sulforhodamine B. Moreover, the survival rate can be obtained by quantifying ATP which is included only in living cells. The amount of ATP can be recognized on the basis of luminescence with luciferase.

Also, as a method using a radiolabeled compound, there is a method in which incorporation of tritiated thymidine into living cells is measured.

In addition to the above, a colony formation method in which growth of cells is observed is also used.

Examples of the method for bringing the adherent cells or the adherent cell population into contact with each test substance in the step (d) include, but are not particularly limited thereto, a method in which the test substance is mixed into a medium containing the adherent cells or the adherent cell population, and a method in which a medium is replaced with a medium in which the test substance is added in advance.

<Method for Screening Substance Having Therapeutic Efficacy for Nervous System Disease>

The method for screening a substance having therapeutic efficacy for a nervous system disease according to one or more embodiments of the present invention includes the following steps (g) to (i):

(g) a step of bringing nerve cells into contact with test substances;

(h) a step of culturing the nerve cells brought into contact with the test substance in the step (g), and nerve cells not brought into contact with the test substances, as a control, by the above culture method for the adherent cells or the adherent cell population; and (i) a step of measuring at least either the cell numbers or the neurite lengths of the nerve cells obtained in the step (h), and selecting a test substance for which the cell number and/or the neurite length of the nerve cells brought into contact with the test substance is higher than that of the control, as a substance having therapeutic efficacy for the nervous system disease.

In the method for screening a substance having therapeutic efficacy for the nervous system disease according to one or more embodiments of the present invention, in the step (h), since the nerve cells brought into contact with the test substances and the nerve cells not brought into contact with the test substances are cultured by using the above culture method for the adherent cells or the adherent cell population, cell death of the nerve cells due to liquid injection upon medium replacement, washing, or the like can be inhibited. Thus, the substance having therapeutic efficacy for the nervous system disease can be confirmed without influence of a decrease in the nerve cells that are not involved in the effect of the test substance.

The therapeutic efficacy in the present disclosure means that a symptom or the like associated with the nervous system disease is alleviated or completely eliminated.

As the nerve cells to be used in the screening method for a substance having therapeutic efficacy for the nervous system disease according to one or more embodiments of the present invention, pluripotent stem cells in which an exogenous nucleic acid (an exogenous nucleic acid in which a nucleic acid encoding Ngn2 is functionally joined to a drug-responsive promotor) is incorporated into the chromosome, and nerve cells obtained by inducing differentiation of the pluripotent stem cells (including cells at a stage in the middle of differentiation) can be used. In the case of using cells derived from the pluripotent stem cells in which the nucleic acid encoding Ngn2 is incorporated into the chromosome, examples of suitable nervous system diseases for which the substance to be screened has therapeutic efficacy include Alzheimer-type dementia.

In one or more embodiments of the present invention, as the nerve cells to be used in the screening method, motor nerve cells and/or pluripotent stem cells in which an exogenous nucleic acid (an exogenous nucleic acid in which a nucleic acid encoding Lhx3, a nucleic acid encoding Ngn2, and a nucleic acid encoding Isl1 are bonded via a 2A sequence and functionally joined to a drug-responsive promotor) is incorporated into the chromosome can also be used.

In the case of using cells derived from the pluripotent stem cells in which a nucleic acid encoding Lhx3, a nucleic acid encoding Ngn2, and a nucleic acid encoding Isl1 are incorporated into the chromosome, a suitable target disease for which the substance to be screened has therapeutic efficacy is a disease caused by deletion or damage of motor nerve cells, and examples of such diseases include amyotrophic lateral sclerosis (ALS), spinal muscular atrophy (SMA), and spinobulbar muscular atrophy (SMBA). Pluripotent stem cells that can be rapidly and synchronously differentiated into motor nerve cells or nerve cells by drug treatment or the like are provided.

Examples of the method for bringing the nerve cells into contact with the test substance in the step (g) include, but are not particularly limited thereto, a method in which the test substance is mixed into a medium containing the nerve cells, and a method in which a medium is replaced with a medium in which the test substance is added in advance.

The screening method may also include a step of inducing differentiation into nerve cells from iPS cells produced from somatic cells of a patient with the nervous system disease or somatic cells of a healthy individual into which a gene mutation causing the nervous system disease is introduced, and culturing the obtained nerve cells by the above culture method for the adherent cells or the adherent cell population, prior to the step (g).

Examples of the method for inducing differentiation from iPS cells into nerve cells include, but are not particularly limited thereto, a method in which an embryoid body (a cell lump containing neural progenitor cells) is formed in a serum-free medium and differentiation is induced (Watanabe K, et al. Nat. Neurosci., 8:288-296, 2005), a method in which embryonic stem cells are cultured on stromal cells and differentiation is induced (Kawasaki H, et al. Neuron, 28:31-40, 2000), a method in which a drug is added onto Matrigel and culture is carried out (Kawasaki H, et al. Neuron, 28:31-40, 2000), and a method in which a low-molecular-weight compound is used as a substitute for cytokine and cells are destined by an extracellular signal (U.S. Pat. No. 5,843,780).

As the method for culturing the nerve cells in the step (h), the nerve cells may be cultured according to the above culture method for the adherent cells.

As the method for measuring the cell number of the nerve cells obtained in the step (h) and in the step (i), the cell number may be measured in the same manner as described above.

In the step (i), the method for measuring the neurite length can be performed through visual observation, or the neurite length may be measured by using a cell image analyzer ("IN Cell Analyzer" manufactured by GE Healthcare Science, "CellInsight" manufactured by Thermo Fisher Scientific, Inc.). At this time, the neurite length may be measured as the area of the neurite on an image of the neurite.

The substance having therapeutic efficacy for the nervous system disease in one or more embodiments of the present invention is a test substance for which the cell number and/or the neurite length of the nerve cells brought into contact with the test substance is higher than that of the control.

Specifically, the cell number and/or the neurite length of the nerve cells brought into contact with the test substance is determined as a high value when being higher than the cell number and/or the neurite length of the control cells by 1.5 times or more, 1.6 times or more, 1.7 times or more, 1.8 times or more, 1.9 times or more, 2.0 times or more, 2.5 times or more, or 3 times or more, and the test substance for which the cell number and/or the neurite length of the nerve cells is determined as a high value is screened as a substance having therapeutic efficacy for the nervous system disease.

<Method for Screening Substance Having Therapeutic Efficacy for Neurodegenerative Disease Due to Protein Misfolding>

One or more embodiments of the present invention provide a method for screening a substance having therapeutic efficacy for a neurodegenerative disease due to protein misfolding, the method including the following steps (j) to (l):

(j) a step of bringing nerve cells derived from a patient with a neurodegenerative disease, into contact with test substances;

(k) a step of culturing the nerve cells derived from the patient with the neurodegenerative disease and brought into contact with the test substances, and nerve cells derived from the patient with the neurodegenerative disease and not brought into contact with the test substances, as a control, by the above culture method for the adherent cells; and (l) a step of measuring amounts of misfolded proteins in the nerve cells that are derived from the patient with the neurodegenerative disease and are obtained in the step (k), or in a medium thereof, and selecting a test substance for which the amount of misfolded proteins in the nerve cells that are derived from the patient with the neurodegenerative disease and are brought into contact with the test substance or in the medium thereof is lower than the amount of the misfolded proteins of the control, as a substance having therapeutic efficacy.

In the method for screening a substance having therapeutic efficacy for the neurodegenerative disease due to protein misfolding according to one or more embodiments of the present invention, since, in the step (k), the nerve cells derived from the patient with the neurodegenerative disease and brought into contact with the test substances and the nerve cells derived from the patient with the neurodegenerative disease and not brought into contact with the test substances are cultured by using the above culture method for the adherent cells or the adherent cell population, cell death of the nerve cells due to liquid injection upon medium replacement, washing, or the like can be inhibited, and the substance having therapeutic efficacy for the neurodegenerative disease due to protein misfolding can be screened without influence of a decrease in the nerve cells that are not involved in the effect of the test substance.

Examples of the neurodegenerative disease due to protein misfolding in one or more embodiments of the present invention include Alzheimer's disease, Parkinson's disease, amyotrophic lateral sclerosis (ALS), and polyglutamine (PolyQ) disease (Huntington's disease, spinocerebellar ataxia type 1, type 2, type 3, type 6, type 7, and type 17, dentatorubropallidoluysial atrophy, spinobulbar muscular atrophy).

The misfolded proteins in one or more embodiments of the present invention are proteins that are not degraded even by a proteolytic system such as ubiquitin-proteasome system or endoplasmic reticulum-associated degradation and are accumulated in a medium or in cells, among proteins misfolded in protein synthesis, and examples of the misfolded proteins include abnormal Huntington proteins, and polyglutamine proteins.

Examples of the method for bringing the nerve cells derived from the patient with the neurodegenerative disease into contact with each test substance in the step (j) include, but are not particularly limited thereto, a method in which the test substance is mixed into a medium in advance, and a method in which the test substance is mixed into a medium containing the nerve cells.

In the step (l), as the method for measuring the amounts of the misfolded proteins in the nerve cells that are derived from the patient with the neurodegenerative disease and are obtained in the step (k), or in the medium of the nerve cells, the amounts of the misfolded proteins may be measured by an ELISA method, which is generally used by a skilled in the art, using a collected culture supernatant after bringing the test substances into contact with iN. Examples of such a method include a method using MSD Abeta 3 plea assay plate (Meso Scale Discovery), Human/Rat β Amyloid ELISA Kit (Wako Pure Chemical Industries, Ltd.), or the like. At this time, a measured value of Aβ (amyloid β protein) 42 may be used as an index, or a value (Aβ42/Aβ40) obtained by dividing the measured value of Aβ42 by a value of Aβ40 may be used as an index. Evaluation may be performed on a protein weight basis under the same conditions, but evaluation may be performed on the basis of a misfolded protein ratio under different conditions.

The substance having therapeutic efficacy for the nervous system disease due to misfolding in one or more embodiments of the present invention is a test substance for which, when the amount (pg/ml) of the misfolded proteins in the nerve cells or in the medium of the nerve cells is measured, the amount (pg/ml) of the misfolded proteins in the nerve cells derived from the patient with the neurodegenerative disease and brought into contact with the test substance or in the medium of the nerve cells is lower than that of the control.

Specifically, the amount (pg/ml) of the misfolded protein in the nerve cells derived from the patient with the neurodegenerative disease and brought into contact with the test substance or in the medium of the nerve cells is determined as a low value when being lower than the amount (pg/ml) of the misfolded proteins in the control cells or in the medium of the control cells, by 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, 1% or less, or 0.5% or less, and the test substance for which the amount (pg/ml) of the misfolded proteins is determined as a low value is screened as a substance having therapeutic efficacy for the nervous system disease due to misfolding.

<Method for Screening Substance Having Therapeutic Efficacy for Alzheimer-Type Dementia>

One or more embodiments of the present invention provide a method for screening a substance having therapeutic efficacy for Alzheimer-type dementia, the method including the following steps (m) to (o):

(m) a step of bringing nerve cells of Alzheimer-type dementia into contact with test substances;

(n) a step of culturing the nerve cells of Alzheimer-type dementia brought into contact with the test substances in the step (m), and nerve cells of Alzheimer-type dementia not brought into contact with the test substances, as a control, by the above culture method for the adherent cells or the adherent cell population within the culture vessel, the culture method including the above liquid injection method; and (o) a step of measuring Aβ42 and/or Aβ40 in media of the nerve cells of Alzheimer-type dementia obtained in the step (n), and selecting a test substance for which a content of Aβ42 in the medium of the nerve cells of Alzheimer-type dementia brought into contact with the test substance and/or a value obtained by dividing the content of Aβ42 by the content of Aβ40 therein (that is, Aβ42 content/Aβ40 content) is lower than that of the control, as a substance having therapeutic efficacy.

In the method for screening a substance having therapeutic efficacy for Alzheimer-type dementia according to one or more embodiments of the present invention, in the step (n), since the nerve cells of Alzheimer-type dementia brought into contact with the test substances and the nerve cells of Alzheimer-type dementia not brought into contact with the test substances are cultured by using the above culture method for the adherent cells or the adherent cell population, cell death of the nerve cells due to liquid injection upon medium replacement, washing, or the like can be inhibited. Thus, the substance having therapeutic efficacy for Alzheimer-type dementia can be confirmed without influence of a decrease in the nerve cells that are not involved in the effect of the test substance.

In one or more embodiments of the present invention, the nerve cells of Alzheimer-type dementia may be any nerve cells as long as the nerve cells are derived from a patient diagnosed with Alzheimer-type dementia, and the types of the nerve cells are not particularly limited.

Examples of the method for bringing the nerve cells of Alzheimer-type dementia into contact with each test substance in the step (m) include, but are not particularly limited thereto, a method in which the test substance is mixed into a medium in advance, and a method in which the test substance is mixed into a medium containing the nerve cells.

The screening method may also include a step of inducing differentiation into nerve cells of Alzheimer-type dementia from induced pluripotent stem cells produced from somatic cells of a patient with Alzheimer-type dementia or somatic cells of a healthy individual into which a gene mutation causing Alzheimer-type dementia is introduced, and culturing the obtained nerve cells of Alzheimer-type dementia by the above culture method for the adherent cells or the adherent cell population, prior to the step (m).

Examples of the method for measuring Aβ42 and/or Aβ40 in the medium of the nerve cells of Alzheimer-type dementia obtained in step (n) in the step (o) include a method using Human/Rat β Amyloid ELISA Kit (Wako Pure Chemical Industries, Ltd.) or the like. At this time, a value (Aβ42/Aβ40) obtained by dividing a measured value of Aβ42 by a value of Aβ40 is used as an index.

The substance having therapeutic efficacy for Alzheimer-type dementia in one or more embodiments of the present invention is a test substance for which, when Aβ42 and/or Aβ40 in the medium of the nerve cells of Alzheimer-type dementia is measured, the content (pg/mL) of Aβ42 in the medium of the nerve cells of Alzheimer-type dementia brought into contact with the test substance and/or a value obtained by dividing the content (pg/mL) of Aβ42 by the content (pg/mL) of Aβ40 therein (that is, Aβ42 content/Aβ40 content) is lower than that for the control.

Specifically, the content (pg/mL) of Aβ42 in the medium of the nerve cells of Alzheimer-type dementia brought into contact with the test substance and/or the value obtained by dividing the content (pg/mL) of Aβ42 by the content (pg/mL) of Aβ40 therein (that is, Aβ42 content/Aβ40 content) is determined as a low value when being lower than the content (pg/mL) of Aβ42 in the medium of the nerve cells of Alzheimer-type dementia not brought into contact with the test substances and/or the value obtained by dividing the content (pg/mL) of Aβ42 by the content (pg/mL) of Aβ40 therein (that is, Aβ42 content/Aβ40 content), by 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, 1% or less, or 0.5% or less, and the test substance for which the content (pg/mL) of Aβ42 and/or the value obtained by dividing the content (pg/mL) of Aβ42 by the content (pg/mL) of Aβ40 is determined as a low value is screened as a substance having therapeutic efficacy for Alzheimer-type dementia.

<Specific Example of Culture Method Upon Inducing Differentiation of iPS Cell-Derived Nerve Cells>

Next, one example of a culture method (feeder culture) upon inducing differentiation of iPS cell-derived nerve cells shown in a process diagram of FIG. 1 to which the liquid injection method according to one or more embodiments of the present invention is applied, will be described.

Sub-steps 3 and 4 and sub-steps 7 and 8 are a washing step of washing the interior of the culture vessel by injecting the washing solution into the culture vessel and sucking the washing solution. As one or more embodiments of the present invention, exemplified is a step of adding 2 mL (in the case of a 6-well plate) of the washing solution to each well of the culture vessel and sucking the washing solution. Sub-steps 3 and 4 and sub-steps 7 and 8 may employ the above liquid injection method.

Sub-steps 5 and 6 are a feeder cell detachment and removal step of injecting the detachment solution and removing the detachment solution. As one or more embodiments of the present invention, exemplified is a step of adding 750 µL (in the case of a 6-well plate) of a CTK solution (a PBS solution obtained by adding 0.25% of trypsin, 1 mg/mL of collagenase, 1 mM of $CaCl_2$, and 20% of KSR) to each well of the culture vessel and then performing incubation within an incubator (at 37° C. for 5 minutes).

Sub-steps 9 to 11 are a cell detachment step of injecting the detachment solution to the adherent cells or the adherent cell population within the culture vessel and sucking the detachment solution in a state where the adherent cells or the adherent cell population is detached. As one or more embodiments of the present invention, exemplified is a step of adding 750 µL (in the case of a 6-well plate) of the detachment solution having an inhibitor for ROCK (ROCK inhibitor), which is one of the intracellular phosphoenzymes, added therein so as to have a final concentration of 10 µM, to each well of the culture vessel, then performing incubation within an incubator (at 37° C. for 10 to 20 minutes), and performing pipetting about 5 times.

Sub-steps 12 to 14 are a centrifugation step of injecting the cell suspension sucked in the cell detachment step into a centrifugation tube and centrifuging the cell suspension with a centrifuge. As one or more embodiments of the present invention, exemplified is a step of adding 8 mL (for one well of a 6-well plate) of the medium having the dissociated cell suspension added therein so as to have a final concentration of the ROCK inhibitor of 10 µM, to a 15 mL-capacity centrifugation tube, and performing centrifugation at 200 g for 5 minutes.

Sub-steps 15 to 19 are a cell number measurement and cell seeding amount adjustment step of removing the supernatant within the centrifugation tube having undergone the centrifugation step, sampling a part of a cell suspension obtained by injecting the medium into the centrifugation tube, measuring the cell number of the cell suspension, and adjusting a cell number or a cell density for seeding the cells on the basis of a result of the measurement. As one or more embodiments of the present invention, exemplified is a step of removing the supernatant within the centrifugation tube having undergone the centrifugation step, suspending the precipitates with 1 mL of the medium in the centrifugation tube, and measuring the cell number of the suspension.

Sub-steps 20 and 21 are a cell seeding step of seeding the cells having a required cell number adjusted in the cell number measurement and cell seeding amount adjustment step into a culture vessel filled with a medium. As one or more embodiments of the present invention, exemplified is a step of seeding the cells into the culture vessel such that a cell density of $4 \times 10^5$ cells/1.5 mL/well (in the case of a 6-well plate) in the medium is achieved, on the basis of a measured cell density. As a plate to be seeded, a plate treated at 37° C. for about 1 hour with a coating liquid obtained by mixing a Synthemax-2 solution (1 mg/mL), a poly-L-lysine solution (0.1 mg/mL), and water in a ratio of 1:1:38 can be used.

Sub-step 22 is a differentiation-inducing culture step of putting the culture vessel having the cells seeded thereinto through the cell seeding step, into a $CO_2$ incubator and performing differentiation-inducing culture. As one or more embodiments of the present invention, exemplified is a step of performing culture in the incubator for 4 or 5 days.

In subculture (Step 2), a medium replacement step of sucking the medium within the culture vessel and injecting a fresh medium into the culture vessel is also performed before returning to Sub-step 2. In Step 2, the step of removing the feeder cells as sub-steps 3 to 6 is omitted.

Next, an example of a differentiation-inducing culture method (feeder-free culture) for iPS cell-derived nerve cells shown in a process diagram of FIG. 2 to which the liquid injection method according to one or more embodiments of the present invention is applied, will be described.

Sub-steps 3 and 4 are a washing step of washing the interior of the culture vessel by injecting the washing solution into the culture vessel and sucking the washing solution. As one or more embodiments of the present invention, exemplified is a step of adding 2 mL of the washing solution to each well of the culture vessel and sucking the washing solution. Sub-steps 3 and 4 may employ the above liquid injection method.

Sub-steps 5 to 7 are a cell detachment step of injecting the detachment solution to the adherent cells or the adherent cell population within the culture vessel and sucking the detachment solution in a state where the adherent cells or the adherent cell population is detached. As one or more embodiments of the present invention, exemplified is a step of adding 750 μL (in the case of a 6-well plate) of the detachment solution having an inhibitor for ROCK (ROCK inhibitor), which is one of the intracellular phosphoenzymes, added therein so as to have a final concentration of 10 μM, to each well of the culture vessel, then performing incubation within an incubator (at 37° C. for 10 to 20 minutes), and performing pipetting about 5 times. Sub-steps 7 and 8 may employ the above liquid injection method.

Sub-steps 8 to 10 are a step of injecting the cell suspension sucked in the cell detachment step into a centrifugation tube and centrifuging the cell suspension with a centrifuge. As one or more embodiments of the present invention, exemplified is a step of adding 8 mL (for one well of a 6-well plate) of the medium obtained by adding the ROCK inhibitor to the suspension of the cells dissociated into single cells such that a final concentration of the ROCK inhibitor is 10 μM, to a 15 mL-capacity centrifugation tube, and performing centrifugation at 200 g for 5 minutes.

Sub-steps 11 to 15 are a cell number measurement and cell seeding amount adjustment step of removing the supernatant within the centrifugation tube having undergone the centrifugation step, sampling a part of a cell suspension obtained by injecting the medium into the centrifugation tube, measuring the cell number of the cell suspension, and adjusting a cell number or a cell density for seeding the cells on the basis of a result of the measurement. As one or more embodiments of the present invention, exemplified is a step of removing the supernatant within the centrifugation tube having undergone the centrifugation step, suspending the precipitates with 1 mL of the medium in the centrifugation tube, and measuring the cell number of the suspension.

Sub-steps 16 and 17 are a cell seeding step of seeding the cells having a required cell number adjusted in the cell number measurement and cell seeding amount adjustment step into a culture vessel filled with a medium. As one or more embodiments of the present invention, exemplified is a step of seeding the cells into the culture vessel such that a cell density of $4\times10^5$ cells/1.5 mL/well (in the case of a 6-well plate) in the medium is achieved, on the basis of a measured cell density. As a plate to be seeded, a plate treated at 37° C. for about 1 hour with a coating liquid obtained by mixing a Synthemax-2 solution (1 mg/mL), a poly-L-lysine solution (0.1 mg/mL), and water in a ratio of 1:1:38 can be used.

Sub-step 18 is a differentiation-inducing culture step of putting the culture vessel having the cells seeded thereinto through the cell seeding step, into a $CO_2$ incubator and performing differentiation-inducing culture. As one or more embodiments of the present invention, exemplified is a step of performing culture in the incubator for 4 or 5 days.

In subculture (Step 2), a medium replacement step of sucking the medium within the culture vessel and injecting a fresh medium into the culture vessel is further performed before returning to sub-step 2.

Figure 2:
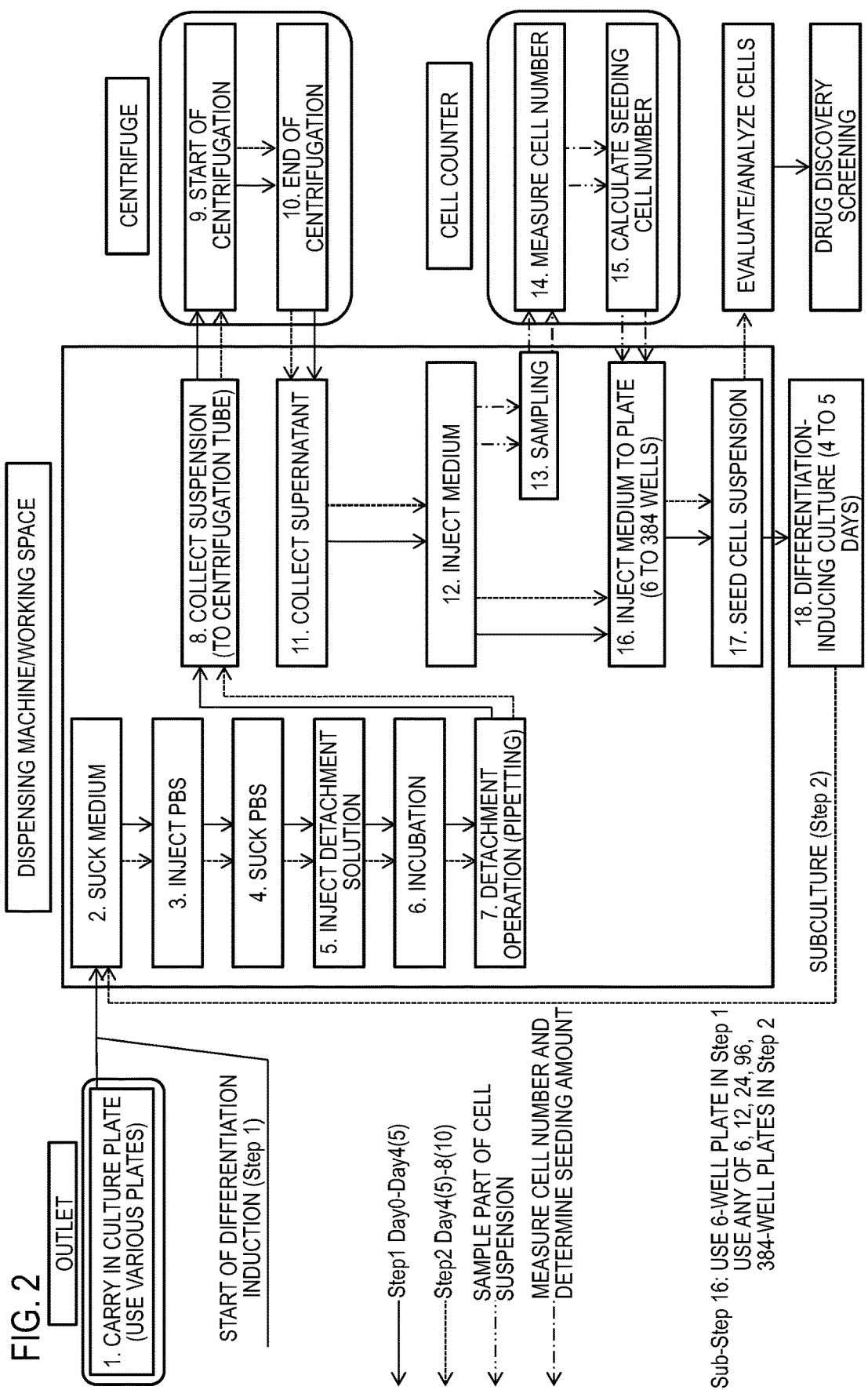
FIG. 2 is a process diagram showing an example of a differentiation-inducing culture method (feeder-free culture) for iPS cell-derived nerve cells.

For example, in the example of the differentiation-inducing culture method (feeder culture) for iPS cell-derived nerve cells shown in the process diagram of FIG. 1 and in the example of the differentiation-inducing culture method (feeder-free culture) for iPS cell-derived nerve cells shown in the process diagram of FIG. 2, the liquid injection method according to one or more embodiments of the present invention is suitably used in injecting the washing solution in the washing step and in injecting the fresh medium in the medium replacement step.

Regarding the adherent cells or the adherent cell population obtained by the above-described method according to one or more embodiments of the present invention, as compared to those by a conventional culture method, damage by a physical load upon injection of a liquid such as a medium or PBS is significantly reduced, and furthermore, the cell number does not decrease due to cell death or variations in the quality of cells after differentiation induction do not occur, since the detachment solution or the additives (for example, a growth factor, a neurotrophic factor family, a differentiation inducing factor, etc.) can be accurately injected in an optimum concentration or in an optimum amount. Thus, cells or a cell population from which correct experiment and evaluation data are easily acquired can be obtained. In addition, even when a sufficient cell number is ensured, there is a possibility that the inherent properties of cells (differentiation potency, proliferative property, homogeneity, and/or stability, hereinafter referred to as inherent cell properties) are impaired due to the damage by the physical load upon injection of the liquid. However, the adherent cells or the adherent cell population obtained by the method according to one or more embodiments of the present invention are cells that sufficiently exhibit their inherent cell properties. Particularly, the adherent cells that are easily detached from the culture vessel, such as nerve cells or iPS cell-derived nerve cells, are easily influenced greatly and negatively by the physical load upon injection of the liquid or the concentrations or the amounts of the detachment solution, the additives, etc., and thus can be collected by using the method according to one or more embodiments of the present invention in a state of sufficiently exhibiting inherent cell properties.

In order to specify the structure of the adherent cells or the adherent cell population obtained by the method according to one or more embodiments of the present invention, it is necessary to find out a new index (a new marker gene, etc.) other than known undifferentiated markers and marker genes of nerve cells. However, competition in development in the life science fields such as iPS cells is very strong, and extremely excessive economical expense and time are required to perform work for specifying the structure of the adherent cells or the adherent cell population at the time of filling the application, and thus it is not practical to specify the structure of the adherent cells or the adherent cell population.

EXAMPLES

Examples 1 and 2 and Comparative Example 1

Liquid Injection Method for iPS Cell-Derived Nerve Cells (Preparation of Human iPS Cell-Derived Nerve Cells)

DNA encoding Ngn2 gene was introduced into human iPS cells (201B7) under control of a tetracycline-responsive promoter by a piggyBack (trademark) transposon vector system, thereby establishing a stable cell line (an iPS cell line induced into iN) in which target DNA was inserted into the genome.

(Maintenance Culture of Human iPS Cell-Derived Nerve Cells)

Examples of a required medium and reagents are shown below.

(1) Maintenance Medium

Stem-Fit (registered trademark) medium (Ajinomoto Co., Inc.), Primate ES cell medium (ReproCELL Incorporated), primate ES/iPS cell medium (Cosmo Bio Co., Ltd.), PSGro hESC/iPSC Medium (System Biosciences, LLC).

(2) Washing Solution

Dulbecco's phosphate buffered saline (D-PBS (−), Na, Ca free).

(3) Detachment Agent

TrypLE Express (Life Technologies "12605010"), or TrypLE Select (Life Technologies "A12859-01").

(4) Detachment Agent Diluent

EDTA/PBS (5) Coating Agent i-Matrix-511 (Nippi, Incorporated), Reprocoat (Repro-CELL Incorporated), and Laminin-5 (ReproCELL Incorporated).

(6) ROCK Inhibitor

Y27632 (Wako Pure Chemical Industries, Ltd. "253-00511").

(7) Trypan Blue Liquid (Wako Pure Chemical Industries, Ltd., NACALAI TESQUE, INC.)

(8) Culture Vessel

Microplates (6-well, 12-well, 24-well, 48-well, 96-well, 384-well), a 35-mm dish, a 60-mm dish, a 100-mm dish (Costar).

(Maintenance Culture Method)

A microplate (6-well, Costar) to which an iMatrix-511 (Nippi, Incorporated) solution was added was heated at 37° C. for 1 hour or longer to be coated. The human iPS cell-derived nerve cells that reached about 80% of a confluent state were washed with a washing solution (PBS) in 1 mL/well, and the washing solution was removed by suction. The detachment solution (0.5×TreypLE Select with EDTA/PBS) was added thereto in 300 µL/well, and heating was performed at 37° C. for about 4 minutes. Thereafter, the detachment solution was removed by suction, the cell was washed with a washing solution (PBS) in 2 mL/well, and the washing solution was removed by suction. Stem-Fit medium was added in 1 mL/well, and the cells were detached with a cell scraper. The cells were suspended in the Stem-Fit medium, and an appropriate amount of the suspension was sampled and stained with the same amount of trypan blue. A cell number was measured with a counter while observing the cells with a microscope using a counting chamber, or was measured by using a cell counter. The suspension was adjusted with Stem-Fit medium so as to have $1.3 \times 10^4$ cells/mL, and was seeded into a 6-well plate in 2 mL/well.

Furthermore, differentiation-inducing culture of the iPS cell-derived nerve cells induced into iN was carried out. An example of the neuronal differentiation-inducing culture method for iPS cells induced into iN will be described.

Examples of a required medium and reagents are shown below.

(1) Nerve Cell Medium

The basal medium is Neurobasal Medium (Gibco, "21103-049") and contains, as additives, L-alanyl-L-glutamine (Glutamax Gibco, "35050-61"), Penicillin/Streptomycin (Gibco, "15140-163"), Doxycycline (Clontech, "631311"), and Human recombinant BDNF CF (R&D Systems, Inc., "248-BD-005/CF"), Human recombinant GDNF CF (R&D Systems, Inc., "212-GD-010/CF"), and Human recombinant NT-3 CF (R&D Systems, Inc., "267-N3-005/CF").

The medium may contain at least one neurotrophic factor family selected from the group consisting of Brain-derived Neurotrophic Factor (BDNF), Glial cell line-derived Neurotrophic Factor (GDNF), and Neurotrophin 3(NT-3).

(2) Washing Solution

Dulbecco's phosphate buffered saline (D-PBS (−), Na, Ca free).

(3) Detachment Solution

TrypLE Express (Life Technologies "12605010"), or TrypLE Select (Life Technologies "A12859-01").

(4) ROCK Inhibitor

Y27632 (Wako Pure Chemical Industries, Ltd. "253-00511").

(5) Culture Vessel

Microplates (6-well, 12-well, 24-well, 48-well, 96-well, 384-well), a 35-mm dish, a 60-mm dish, a 100-mm dish (Costar).

(Culture Method)

(1) Washing is performed by adding 2 mL of the washing solution to each well of a culture vessel in which human iPS cell-derived nerve cells which are adherent (adhesive) cells or an adherent (adhesive) cell population is cultured.

(2) The detachment solution having an inhibitor for ROCK (ROCK inhibitor), which is one of the intracellular phosphoenzymes, added therein so as to have a final concentration of 10 µM is added in 750 µL (in the case of a 6-well plate) to each well of the culture vessel, and then incubation is performed within an incubator (at 37° C. for 10 to 20 minutes) to dissociate the cells forming colonies into single cells.

(3) The culture vessel is taken out from the incubator and pipetting is performed 5 times for each well to completely dissociate the cells.

(4) The nerve cell medium having the ROCK inhibitor added therein so as to have a final concentration of 10 µM is dispensed in 8 mL (for one well) into a 15-mL centrifugation tube.

(5) The dissociated cell suspension in (3) is added to the nerve culture medium, and centrifugation is performed at 200 g for 5 minutes.

(6) After the centrifugation, the supernatant was removed by suction, the precipitates are suspended with 1 mL of the medium, and a cell number is measured.

(7) The cells are seeded into a culture vessel such that a cell density of $4 \times 10^5$ cells/1.5 mL/well in the medium is achieved, on the basis of a cell density measured in (6).

(8) Culture is carried out in an incubator for 4 or 5 days. During the period, the medium is not replaced.

(Induction of Mature Nerve Cells)

(9) The culture vessel described in (7) is taken out from the incubator, the detachment solution having the ROCK inhibitor added therein so as to have a final concentration of 10 μM is added in 750 μL (in the case of a 6-well plate) to each well, and incubation is performed at 37° C. for about 25 minutes to dissociate the cells into single cells.

(10) A required amount of the medium is added to a centrifugation tube (about 7 mL for one well of a 6-well plate).

(11) The culture vessel is taken out from the incubator, and pipetting is performed 10 times for each well to completely dissociate the cells.

(12) The cells are suspended into the medium prepared in (10).

(13) Centrifugation is performed (200 g, 5 minutes).

(14) The supernatant is removed by suction, the cells are suspended with 1 mL of the nerve cell medium, and a cell number is measured.

(15) The suspension is adjusted with the medium prepared in (14) so as to have a cell density of $3 \times 10^5$ cells/1.5 mL/well, and is seeded into a culture vessel (as the culture vessel, 6-well, 12-well, 24-well, 48-well, 96-well, and 384-well are selectively used as necessary).

(16) The cells are cultured in an incubator at 37° C. for 4 or 5 days, and then are subjected to an experiment.

(Experiment for Establishing Liquid Injection Method)

Next, an experiment for establishing the liquid injection method according to one or more embodiments of the present invention was carried out by using the cultured adherent cells.

In the experiment apparatus shown in a partially cross-sectional schematic diagram of FIG. 3, iPS cell-derived nerve cells (cells at the 8th to 10th day after differentiation induction) 1 are attached to the bottom surface 2A of the multi-well plate 2 which is a culture vessel.

The multi-well plate 2 is fixed to the tilting table 4 in a state where the multi-well plate 2 is placed on the tilting table 4, and the tilting table 4 can hold the multi-well plate 2 in a horizontal state or in a state where the multi-well plate 2 is tilted around the horizontal support axis 5 by a tilt angle X (°) from the horizontal state.

After the multi-well plate 2 is tilted at a predetermined tilt angle by the tilting table 4, the tip end of the pipette tip 8 is located on the wall surface 2B at the lower side of a well into which a liquid is to be injected.

Next, a phosphate-buffered saline (PBS) 3 is injected into the multi-well plate 2 from the syringe pump 6 via the pipe 7 with the pipette tip 8.

The phosphate-buffered saline (PBS) 3 coming out from the pipette tip 8 reaches the nerve cells 1 attached to the bottom surface 2A, via the wall surface 2B of the multi-well plate 2.

That is, the PBS 3 is injected toward the nerve cells 1 attached to the bottom surface 2A, via the wall surface 2B on which the nerve cells 1 are not present.

(Results)

The experiment was carried out such that the tilt angle X (°) set by the tilting table 4 and the linear velocity Y (mm/s) at the tip end of the pipette tip 8 were changed as shown in Table 1.

The item to be evaluated in the experiment is the cell survival rate of the nerve cells 1. Specifically, the ratio of the living cell number of the nerve cells 1 attached to the bottom surface 2A of the well after injection relative to the living cell number of the nerve cells 1 attached to the bottom surface 2A of the well before injection was measured, and this ratio was used as a cell survival rate.

A condition of the tilt angle and the liquid injection linear velocity under which the cell survival rate in the experiment was not less than 90% was determined as acceptable.

Under the conditions of Example 1 using a 24-well plate and in the injection experiment of Example 2 using a 96-well plate, a high cell survival rate of not less than 90% was obtained under either condition and satisfied the acceptance criterion.

On the other hand, it was found that even at the same tilt angle, when the liquid injection linear velocity was adjusted as in Comparative Example 1, the cell survival rate was 50 to 80% and significantly decreased as compared to the result at the same tilt angle in Example 1, and the cell survival rate further decreased when the linear velocity was made higher than that in Comparative Example 1.

The results in Example 1 are results of measurement of the maximum linear velocity at which survival of 90% or more of the cells was confirmed at each tilt angle when the 24-well plate was used, and the results in Example 2 are results of such measurement when the 96-well plate was used. Therefore, for example, even when the linear velocity is adjusted to less than 123 mm/s at a tilt angle of 0° in Example 1, the cell survival rate is not less than 90% (the same applies even under other conditions of Examples 1 and 2).

TABLE 1

| | | Tilt angle X (°) | | | | | | | Remarks |
| --- | --- | --- | --- | --- | --- | --- | --- | --- | --- |
| | | 0 | 5 | 10 | 20 | 30 | 35 | 40 | |
| Linear velocity Y (mm/s) | Ex. 1 | 123 | 132 | 132 | 185 | 264 | 291 | 326 | iN, 24-well plate were used |
| | Ex. 2 | 97 | 106 | 106 | 106 | 203 | 264 | 317 | iN, 96-well plate were used |
| | Comp. Ex. 1 | 150 | 176 | 194 | 247 | 291 | 317 | 353 | iN, 24-well plate were used |

Figure 4:
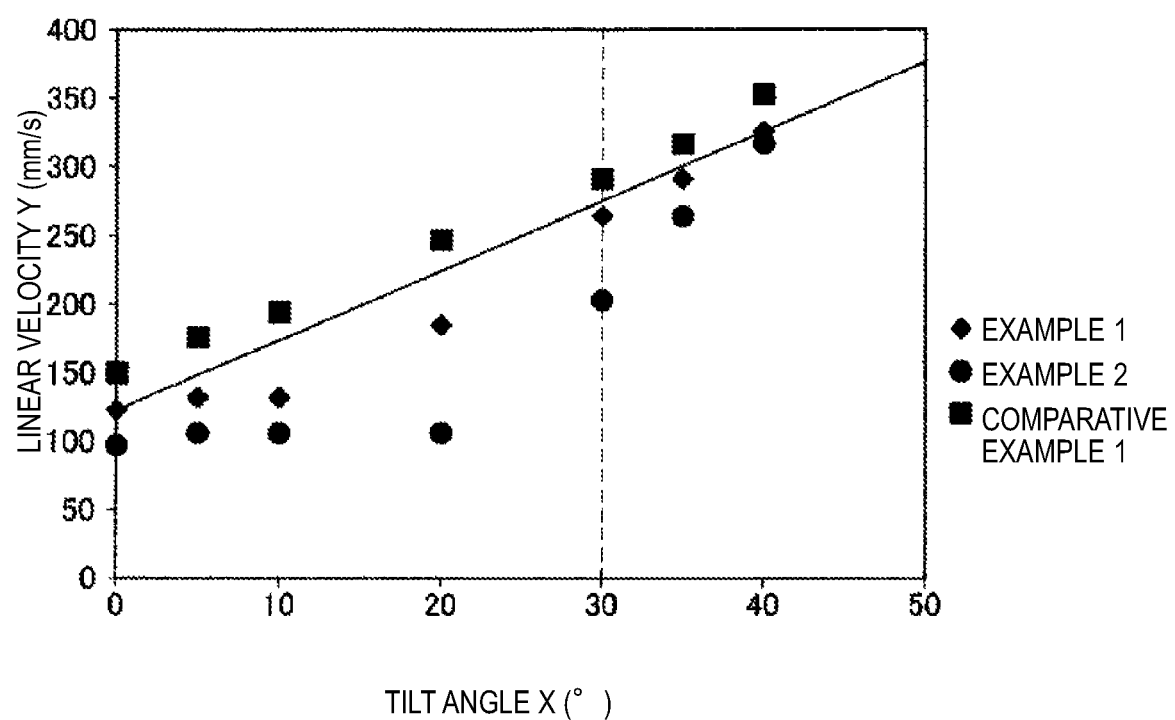
FIG. 4 is a diagram showing the relationship between a tilt angle X and a linear velocity Y.

A straight line that is shown in FIG. 4 obtained by graphing the relationship between the tilt angle X and the linear velocity Y in Example 1 in Table 1 is Y=5.075X+123.

Thus, it is recognized that if the following relationship is satisfied:

$$Y \leq 5.075X + 123 \quad \text{(formula 1)},$$

cell death of adherent cells or adherent cell population can be assuredly prevented, and the operation efficiency can be maximized while improving the survival rate of the adherent cells, by increasing the linear velocity Y as much as possible within the range of the inequality of the formula 1.

From the results of Table 1 and FIG. 4, it is recognized that the linear velocity Y (mm/s) can be made higher with the 24-well plate (culture area: 1.9 cm$^2$) than with the 96-well plate (culture area: 0.35 cm$^2$). Thus, it is recognized that it is better to increase the culture area in order to improve the operation efficiency.

For example, in order to improve the operation efficiency, the culture area may be 0.35 cm$^2$ (96-well plate) rather than 0.084 cm$^2$ (384-well plate), or may be 1.0 cm$^2$ (48-well plate) or 1.9 cm$^2$ (24-well plate).

From the results of Table 1 and FIG. 4, it is recognized that the linear velocity Y (mm/s) can be made higher with the radius (R) of an arc (curvature) of each well of the 24-well plate than with the radius (R) of an arc (curvature) of each well of the 96-well plate. Thus, in order to improve the operation efficiency, the radius of the arc (curvature) of each well may be lengthened.

For example, in order to improve the operation efficiency, the arc radius may be 3.3 mm (96-well plate) rather than 1.2 mm (384-well plate), or may be 6.2 mm (48-well plate) or 8.1 mm (24-well plate).

From the results of Table 1 and FIG. 4, it is recognized that the tilt angle X (°) is set as X≤40° in order to assuredly prevent overflowing of the injected liquid from the culture vessel, and cell death is rapidly decreased when the tilt angle X (°) exceeds 30° (see a broken line in the drawing).

Thus, it was found that the tilt angle X may be within the range of not less than 30° and not greater than 40° (that is, 30°≤X≤40° in order to prevent overflowing of the injected liquid from the culture vessel and in order to increase the operation efficiency as much as possible while improving the cell survival rate. It was found that it is possible to substitute the value of the tilt angle X as a result of tilting in this manner into the inequality of the formula 1 and to set the linear velocity Y to be as high as possible within the range of the inequality of the formula 1.

Example 3

The same liquid injection experiment as in Example 1 was carried out by using 293FT cells as the adherent cells.

(Adherent Cells)

293FT cells (Cosmo Bio Co., Ltd.)

(Maintenance Culture of 293FT Cells)

Examples of a required medium and reagents are shown below.

(1) Maintenance Medium

DMEM (low glucose: 1 g/L) (product code "12-707F")

(2) Medium-added Factor

Inactivated FCS, L-Glutamine, Penicillin-Streptomycin (3) Washing Solution

Dulbecco's phosphate buffered saline (D-PBS (−), Na, Ca free)

(4) Trypan Blue Liquid (Wako Pure Chemical Industries, Ltd., NACALAI TESQUE, INC.)

(Culture Method)

The 293FT cells cryopreserved in a concentration of $1\times10^7$ cell/mL are thawed in a warm bath at 37° C., are suspended in 8 mL of D-PBS, and are centrifuged at 200 g for 5 minutes. After the centrifugation, the supernatant is removed, 1 mL of the medium is added, and a cell number is measured. The cells are seeded in $1\times10^5$ cells/mL per well of a culture vessel, culture is carried out at a temperature of 37° C. in a carbon dioxide concentration of 5.0% or less, and the 293FT cells that reach 80% or more of a confluent state are subjected to an experiment.

(Results)

When the experiment in which liquid injection was performed with the linear velocity and the tilt angle changed stepwise similarly to Example 1 was carried out a plurality of times by using the 293FT cells, it was confirmed that the cell survival rate became not less than 90% by adjusting the linear velocity Y (mm/s) and the tilt angle X within the range satisfying the inequality of the formula 1 in each time of the experiment.

Example 4

The same liquid injection experiment as in Example 1 was carried out by using neural stem cells as the adherent cells.

(Adherent Cells)

Neural stem cells (CDI, product number NRC-100-010-001)

(Differentiation Culture of Neural Stem Cells)

Examples of a required medium and reagents are shown below.

(1) Differentiation medium: iCell Neurons Maintenance Medium (CDI: product number NRC-100-121-001)

(2) Medium-added factor: iCell Neurons Medium Supplement (CDI: product number NRC-100-031-001)

(3) Laminin (Sigma-Aldrich L-2020)

(4) Poly-L-Ornithine (Sigma-Aldrich P4957)

(5) Trypan blue liquid (Wako Pure Chemical Industries, Ltd., NACALAI TESQUE, INC.)

(Culture Method)

The neural stem cells cryopreserved in a concentration of $1\times10^6$ cell/mL are thawed in a warm bath at 37° C. and are suspended in 1 mL of the differentiation medium. A vessel in which the neural stem cells have been contained is rinsed with 1 mL of the differentiation medium, and the used differentiation medium is added to the cell suspension. Furthermore, 8 mL of the differentiation medium was added to the cell suspension. The number of the cells contained in the cell suspension stained with trypan blue is measured, the cells are seeded in $8\times10^4$ cells/mL/24 wells per well of a culture vessel, culture is carried out at a temperature of 37° C. in a carbon dioxide concentration of 5.0% for 8 days, and differentiated nerve cells are subjected to an experiment.

(Results)

When the experiment in which liquid injection was performed with the linear velocity and the tilt angle changed stepwise similarly to Example 1 was carried out a plurality of times by using the neural stem cells, it was confirmed that the cell survival rate became not less than 90% by adjusting the linear velocity Y (mm/s) and the tilt angle X within the range satisfying the inequality of the formula 1 in each time of the experiment.

Examples 1 to 4 described above are representative examples. In addition to Examples 1 to 3, when an experiment in which the types of the nerve cells, the pipette tip, and the well plate were changed to different ones, respectively, and liquid injection was performed with the linear velocity and the tilt angle changed stepwise similarly to Example 1 was carried out a plurality of times, it was confirmed that the cell survival rate became not less than 90% by adjusting the linear velocity Y (mm/s) and the tilt angle X within the range satisfying the inequality of the formula 1 in each time of the experiment.

The liquid injection method according to one or more embodiments of the present invention as described above is a method that can significantly inhibit cell death due to liquid injection as described above, and thus is suitably used in replacing the medium or in injecting the washing solution in the culture method for the adherent cells or the adherent cell population.

For example, in maintenance culture of human iPS cells, a maintenance medium (Stem-Fit AK03, Stem-Fit AK03N: Ajinomoto Co., Inc.) within a culture vessel (6-well plate: Costar, Corning Incorporated) is removed by suction, the cells are washed by injecting a washing solution D-PBS(−) (NACALAI TESQUE, INC.) in 1.0 mL per well using the liquid injection method according to one or more embodiments of the present invention, and then the washing solution is removed by suction.

Next, a detachment agent (0.5×TrepLE Select with EDTA/PBS, TrypLE Express: Life Technologies) containing a $\frac{1}{1000}$ amount of a ROCK inhibitor (Y-27632: NACALAI TESQUE, INC., Wako Pure Chemical Industries, Ltd.) is injected in 300 μL per well by using the liquid injection method according to one or more embodiments of the present invention, and the culture vessel is allowed to stand at a temperature of 37° C. in a $CO_2$ concentration of 5.0% for about 4 minutes. Thereafter, the detachment solution is removed by suction, the cells are washed by injecting a washing solution D-PBS(−) (NACALAI TESQUE, INC.) in 2.0 mL per well using the liquid injection method according to one or more embodiments of the present invention, and then the washing solution is removed by suction.

Thereafter, the maintenance medium containing a $\frac{1}{1000}$ amount of Y-27632 is injected in 1 mL/well by using the liquid injection method according to one or more embodiments of the present invention, and the cells are detached with a cell scraper. Thereafter, pipetting is performed 5 times thereby to make the cells in the form of colony into single cells.

The detached cell suspension is injected into a 50 mL-capacity centrifugation tube (Falcon, Corning Incorporated) containing a predetermined amount of the maintenance medium, the cell suspension and trypan blue are mixed in a ratio of 1:1 to stain the cells, the mixture is injected into a counting chamber, and a living cell number is measured with a microscope. The cell suspension is adjusted with the maintenance medium such that the cell concentration is $1.3 \times 10^4$ cells/well. Thereafter, the cell suspension is seeded in 1.5 mL/well into a culture vessel (6-, 12-, 24-, 48-, 96-, 384-multi-well plates: Costar, Corning Incorporated) in which each well bottom is coated with 2 mL of i-Matrix-511 (Nippi, Incoporated) in advance, and then culture is carried out at a temperature of 37° C. in a $CO_2$ concentration of 5.0% until about 80% of a confluent state is achieved.

In differentiation-inducing culture of iPS cell-derived nerve cells (iN) to be used in Examples 1 and 2, the maintenance medium within a culture vessel (6-, 12-, 24-, 48-, 96-, 384-multi-well plates: Costar, Corning Incorporated) is removed by suction, the cells are washed by injecting a washing solution D-PBS(−) (NACALAI TESQUE, INC.) thereto in 1.0 mL per well using the liquid injection method according to one or more embodiments of the present invention, and the washing solution is removed by suction. Thereafter, a detachment agent (TrypLE Select, TrypLE Express: Life Technologies) containing a $\frac{1}{1000}$ amount of a ROCK inhibitor (Y-27632: NACALAI TESQUE, INC., Wako Pure Chemical Industries, Ltd.) is injected in 750 μL per well by using the liquid injection method according to one or more embodiments of the present invention, and the culture vessel is allowed to stand at 37° C. in 5.0% $CO_2$ for 12 to 17 minutes to detach the cells. Thereafter, pipetting is performed 5 times to make the cells into single cells.

By using the liquid injection method according to one or more embodiments of the present invention (the tilt angle of the culture vessel is 40°) in executing the above step, differentiation-inducing culture of iPS cells in a undifferentiated state into nerve cells (iN) can be efficiently carried out while cell death is inhibited.

In this case, the suspension of the detached cells is injected into a 50 mL-capacity centrifugation tube (Falcon, Corning Incorporated) containing a predetermined amount of an NBD 0.5 medium (containing Neuro Basal Medium (Gibco), B-27 Supplement Minus vitamin A (Gibco), Glutamax (Gibco), recombinant-GDNF (R&D Systems, Inc.), recombinant-BDNF (R&D Systems, Inc.), recombinant-NT3 (R&D Systems, Inc.), a ROCK inhibitor Y-27632 (NACALAI TESQUE, INC., Wako Pure Chemical Industries, Ltd.), and Doxycycline (Clontech)), and centrifugation is performed with a centrifuge (Rotanta 460: Hettich) at 200 g for 5 minutes to separate the suspension into the cells and a supernatant. The supernatant is removed by suction, and a predetermined amount of the NBD 0.5 medium is added to the resultant to suspend the cells. Then, a living cell number is measured with a cell number measuring device (Cedex HiRes: Roche), the cell suspension is adjusted with the NBD 0.5 medium such that the cell concentration is $4.0 \times 10^5$ cells/well, and the adjusted cell suspension is seeded in 1.5 mL per well into a culture vessel (6-, 12-, 24-, 48-, 96-, 384-multi-well plates: Costar, Corning Incorporated) in which each well bottom is coated in advance with 1 mL of a coating agent prepared with Synthemax-II (Corning International, Inc.), a poly-L-lysine solution (Sigma-Aldrich), and sterile water (NACALAI TESQUE, INC.) in a ratio of 1:1:38, and then culture is carried out at a temperature of 37° C. in a $CO_2$ concentration of 5.0% for 4 to 5 days.

Furthermore, in differentiation-inducing culture of iPS cell-derived nerve cells (iN) to be used in Examples 1 and 2, the NBD 0.5 medium within a culture vessel (6-, 12-, 24-, 48-, 96-, 384-multi-well plates: Costar, Corning Incorporated) is removed by suction, the cells are washed by injecting a washing solution D-PBS(−) (NACALAI TESQUE, INC.) thereto in 1.0 mL per well using the liquid injection method according to one or more embodiments of the present invention, and the washing solution is removed by suction. Thereafter, a detachment agent (TrypLE Select, TrypLE Express: Life Technologies) containing a $\frac{1}{1000}$ amount of a ROCK inhibitor (Y-27632: NACALAI TESQUE, INC., Wako Pure Chemical Industries, Ltd.) is injected in 750 μL per well by using the liquid injection method according to one or more embodiments of the present invention, and the culture vessel is allowed to stand at 37° C. for 25 minutes to detach the cells. Thereafter, pipetting is performed 10 times to make the cells in the form of colony into single cells. As described above, differentiation-inducing culture of iPS cells in a undifferentiated state into nerve cells (iN) can be efficiently carried out, while cell death is inhibited, by using the liquid injection method according to one or more embodiments of the present invention (the tilt angle of the culture vessel is 40').

The suspension of the cells detached as described above is injected into a 50 mL-capacity centrifugation tube (Falcon, Corning Incorporated) containing a predetermined amount of a DBA 0.5 medium, and centrifugation is performed with a centrifuge (Rotanta 460: Hettich) at 200 g for 5 minutes to separate the suspension into the cells and a supernatant. The supernatant is removed by suction, and a predetermined amount of the NBD 0.5 medium is added to the resultant to suspend the cells. Then, a living cell number is measured with a cell number measuring device (Cedex HiRes: Roche), the cell suspension is adjusted with the NBD 0.5 medium such that $3.0 \times 10^5$ cells/well is achieved, and the adjusted cell suspension is seeded in 1.5 mL per well into a culture vessel (6-, 12-, 24-, 48-, 96-, 384-multi-well plates: Costar, Corning Incorporated) coated in advance per well with 1 mL of a coating agent prepared with Synthemax-II (Corning International, Inc.), a poly-L-lysine solution (Sigma-Aldrich), and sterile water (NACALAI TESQUE, INC.) in a ratio of 1:1:38, and then culture is carried out at a temperature of 37° C. in a $CO_2$ concentration of 5.0% for 4 to 5 days.

As described in Examples 1 and 2, the method can significantly inhibit cell death of iPS cell-derived nerve cells (iN) due to liquid injection, and thus is suitably used in medium replacement performed for extending a culture period, in investigating effects such as growth stimulation and toxicity of various compounds to cells, in injecting a washing solution for washing adherent cells or an adherent cell population on a culture substrate surface before adding a compound, and in adding a compound.

The liquid injection method according to one or more embodiments of the present invention can be executed in a commercially available dispensing device or automatic culture device. When the liquid injection method according to one or more embodiments of the present invention is executed in the dispensing device or automatic culture device, a suitable pipetting operation is enabled regardless of the type of adherent cells or an adherent cell population, and it is possible for any person to easily culture adherent cells which easily die, such as nerve cells.

In development of a therapeutic drug, a medicine candidate material, and a food candidate material, when a candidate material is screened, cells are damaged due to contact between test substances and the cells, so that the cells may easily die. By performing a pipetting operation by which such cells do not die, the cells can be left in an adhered state, so that it is possible to accurately analyze influence of the candidate material on the cells.

Example 5

Method for Screening Growth Factor or Nutritional Factor Useful for Culture of Adherent Cells or Adherent Cell Population The culture method for adherent cells or an adherent cell population using the liquid injection method according to one or more embodiments of the present invention allows the cells to be efficiently cultured while significantly inhibiting cell death due to liquid injection as described above, and thus is suitably used in a method for screening a growth factor or a nutritional factor useful for culture of adherent cells. For example, such a method can be executed as follows.

(1) Test Substance

Insulin, transferrin, interleukin 6

(2) Step

The human iPS cell-derived nerve cells (iN) described in Example 1 are prepared as adherent cells or an adherent cell population, and the nerve cells brought into contact with the test substances and the nerve cells not brought into contact with the test substances, as a control, are cultured in a $CO_2$ incubator for 2 days. Then, the culture solutions are sucked, and a medium is injected by the above liquid injection method.

The cell numbers of the obtained nerve cells are measured with a microscope (eyepiece ×10, objective ×20) or a cell counter, and a test substance for which the cell number of the nerve cells brought into contact with the test substance is higher than that of the control is selected as a growth factor or a nutritional factor useful for culture of the nerve cells.

Nerve Growth Factor (NGF) can be used as a positive control.

Example 6

Method for Evaluating Toxicity to Adherent Cells or Adherent Cell Population

The culture method for adherent cells or an adherent cell population using the liquid injection method according to one or more embodiments of the present invention allows the cells to be efficiently cultured while significantly inhibiting cell death due to liquid injection, and thus is suitably used in a method for evaluating toxicity to adherent cells. For example, such a method can be executed as follows.

(1) Test Substance

Colchicine (Tokyo Chemical Industry Co., Ltd.), Vindesine (Sigma-Aldrich)

(2) Step (Induction of Neurite Elongation and Contact of Test Drugs to Nerve Cells) The nerve cells described in Example 1 are prepared as adherent cells or an adherent cell population, seeded into a 96-well plate in 2000 cells/well/50 µL, and incubated for 72 hours. After 72 hours, the medium is sucked, and each test drug diluted with the medium in a required concentration so as to achieve 50 ng/mL is injected in 50 µL/well by the above liquid injection method.

As a control, the medium that does not contain any test drug and is injected by the above liquid injection method is prepared.

After culture for 24 hours, immunostaining is performed by using a method known to a person skilled in the art, the number of cells expressing β-tublin, map2, and Vglut is measured by using a cell image analyzer (IN Cell Analyzer, CellInsight), and a test substance for which the cell number of the nerve cells brought into contact with the test substance is lower than that of the control is selected as a substance having toxicity to the nerve cells.

Example 7

Method for Screening Substance Having Therapeutic Efficacy for Nervous System Disease The culture method for adherent cells by using the liquid injection method according to one or more embodiments of the present invention allows the cells to be efficiently cultured while significantly inhibiting cell death due to liquid injection as described above, and thus is suitably used in a method for screening a substance having therapeutic efficacy for a nervous system disease. For example, such a method can be executed as follows.

(1) Test Substances

Glucagon, casein, egg protein (2) Step

The nerve cells described in Example 1 are prepared as adherent cells or an adherent cell population, and the nerve cells brought into contact with the test substances and the nerve cells not brought into contact with the test substances, as a control, are cultured in a $CO_2$ incubator for 2 days. Then, the culture solutions are sucked, and a medium is injected by the above liquid injection method.

The cell numbers of the obtained nerve cells are measured with a microscope (eyepiece ×10, objective ×20) or a cell counter, and a test substance for which the cell number of the nerve cells brought into contact with the test substance is higher than that of the control is selected as a substance having therapeutic efficacy for the nervous system disease.

In addition, a living cell number survival rate of each test substance is calculated by using a cell image analyzer (IN Cell Analyzer manufactured by GE Healthcare Science, CellInsight manufactured by Thermo Fisher Scientific, Inc.) with the value of untreated cells defined as 100%. A test substance for which the cell survival rate is higher than that of the control is selected as a substance having therapeutic efficacy for the nervous system disease.

Furthermore, the area of a neurite on an image of the neurite is measured as a neurite length by using the cell image analyzer, and a test substance for which the neurite length is larger than that of the control is selected as a test substance having therapeutic efficacy for the nervous system disease.

Example 8

Method for Screening Substance Having Therapeutic Efficacy for Neurodegenerative Disease Due to Misfolding The culture method for adherent cells or an adherent cell population using the liquid injection method according to one or more embodiments of the present invention allows the cells to be efficiently cultured while significantly inhibiting cell death due to liquid injection as described above, and thus is suitably used in a method for screening a substance having therapeutic efficacy for a neurodegenerative disease due to misfolding. For example, such a method can be executed as follows.

(1) Test Substance
Trehalose
(2) Step
(a) Count of Aggregates

Inductive motor nerve cells (iMN) are established in which exogenous nucleic acids (a nucleic acid encoding Lhx3, a nucleic acid encoding Ngn2, and a nucleic acid encoding Isl1) are introduced and expressed in induced pluripotent stem cells (iPS cells) derived from a patient with amyotrophic lateral sclerosis (ALS) by the same method as the method for establishing pluripotent stem cells induced into iN as described in Example 1. The above liquid injection method is used in sucking the culture solution and injecting a fresh medium.

iMN to be subjected to an experiment is prepared by culture in the nerve culture medium, and adherent cells brought into contact with the test substance and adherent cells or an adherent cell population not brought into contact with the test substance as a control are cultured in a $CO_2$ incubator for 3 days. Then, aggregates formed due to misfolding are detected by using a transport transient permeabilization kit (Life Technologies, Gaithersburg, Md.), and cells having the aggregates are manually counted under a fluorescence microscope.

(b) Measurement of Misfolded Proteins

Next, the amount of misfolded proteins in the medium in which the aggregates are observed or in the nerve cells is measured by using MSD Abeta 3 plea assay plate (Meso Scale Discovery), Human/Rat β Amyloid ELISA Kit (Wako Pure Chemical Industries, Ltd.), or the like. At this time, a measured value of Aβ (amyloid β protein) 42 may be used as an index, or a value (Aβ42/Aβ40) obtained by dividing the measured value of Aβ42 by a value of Aβ40 may be used as an index.

The amount of misfolded proteins in the nerve cells derived from the patient with the neurodegenerative disease or in the medium of the nerve cells is measured as described above, and a test substance for which the amount of the misfolded proteins in the medium of the nerve cells derived from the patient with the neurodegenerative disease and brought into contact with the test substance or in the nerve cells is lower than that of the control is selected as a test substance having therapeutic efficacy.

Example 9

Method for Screening Substance Having Therapeutic Efficacy for Alzheimer-Type Dementia The culture method for adherent cells using the liquid injection method according to one or more embodiments of the present invention allows the cells to be efficiently cultured while significantly inhibiting cell death due to liquid injection as mentioned above, and thus is suitably used in a method for screening a substance having therapeutic efficacy for Alzheimer-type dementia. For example, such a method can be executed as follows.

(1) Test Substances
Pyrinixin, clofibrate
(2) Step

Inductive nerve cells (iN) are established in which Ngn2 gene is introduced and expressed in induced pluripotent stem cells (iPS cells) derived from a patient with Alzheimer-type dementia. The above liquid injection method is used in sucking the culture solution and injecting a fresh medium.

iN to be subjected to an experiment is prepared by culture in the nerve cell medium, 0.01 to 0.5 mM of each test substance is added into the nerve cell medium, and iN brought into contact with the test substance and iN not brought into contact with the test substance as a control are treated in a $CO_2$ incubator for 16 hours.

After end of the treatment, an Aβ40 value and an Aβ42 value are measured by an ELISA method (Human/Rat β Amyloid (42) ELISA Kit Wako (Wako Pure Chemical Industries, Ltd.)), which is generally used by a person skilled in the art, using the collected culture supernatant. A value (Aβ42/Aβ40) obtained by dividing the Aβ42 value by the Aβ40 value is calculated from the obtained data.

A test substance for which Aβ42/Aβ40 in the medium of iN brought into contact with the test substance is lower than that of the control is selected as a substance having therapeutic efficacy for Alzheimer-type dementia.

Although the disclosure has been described with respect to only a limited number of embodiments, those skilled in the art, having benefit of this disclosure, will appreciate that various other embodiments may be devised without departing from the scope of the present invention. Accordingly, the scope of the present invention should be limited only by the attached claims.

DESCRIPTION OF THE REFERENCE CHARACTERS 1 iPS cell-derived nerve cell (adherent cell)
2 multi-well plate (culture vessel)
2A bottom surface
2B wall surface
3 PBS (liquid)
4 tilting table
5 horizontal support axis (horizontal axis)
6 syringe pump
7 pipe
8 pipette tip
9 automated apparatus
10 pipetter
O control device

What is claimed is:

1. A method for culturing adherent cells, the method comprising:
    sucking a medium out of a culture vessel;
    tilting the culture vessel around a horizontal axis at a tilt angle (X°) of greater than 0° to 50° or less, wherein adherent cells are adhered to the culture vessel;
    injecting a fresh medium into the culture vessel at a predetermined linear velocity (Y mm/s) via a wall surface of the culture vessel tilted at the tilt angle (X°);
    culturing the adherent cells; and
    washing an interior of the culture vessel by injecting a washing solution into the culture vessel and sucking the washing solution out of the culture vessel, wherein the tilt angle (X°) and the linear velocity (Y mm/s) satisfy the following:

$$Y \leq 5.075X + 123 \quad \text{(formula 1)}.$$

2. The method according to claim 1, wherein the tilt angle (X°) is 30° or more to 40° or less.

3. The method according to claim 1, wherein the washing is performed by injecting the washing solution into the culture vessel at the linear velocity (Y mm/s) via the wall surface of the culture vessel tilted at the tilt angle (X°).

4. The method according to claim 1, further comprising:
    injecting a detachment solution to the adherent cells in the culture vessel;
    sucking the detachment solution comprising the adherent cells detached from the culture vessel;
    transferring the detachment solution into a centrifugation tube, and centrifuging the detachment solution;
    removing a supernatant of the detachment solution in the centrifugation tube, counting the number of the adherent cells by sampling a part of a cell suspension obtained by adding a fresh medium into the centrifugation tube, and adjusting the number or a density of the adherent cells; and
    seeding the adherent cells having the adjusted number or density into a culture vessel filled with a fresh medium.

5. The method according to claim 1, wherein the culture vessel is one of a multi-well plate, a microplate, a micro-well plate, and a multi-dish.

6. The method according to claim 1, wherein the linear velocity (Y mm/s) satisfies the following: 97 mm/s ≤ Y ≤ 326 mm/s.

7. The method according to claim 5, wherein the linear velocity (Y mm/s) satisfies the following: 97 mm/s ≤ Y ≤ 326 mm/s.

* * * * *